(12) United States Patent
Cance et al.

(10) Patent No.: US 8,314,150 B2
(45) Date of Patent: Nov. 20, 2012

(54) KINASE PROTEIN BINDING INHIBITORS

(76) Inventors: William G. Cance, Orchard Park, NY (US); Vita Golubovskaya, Orchard Park, NY (US); David A. Ostrov, Gainesville, FL (US)

( * ) Notice: Subject to any disclaimer, the term of this patent is extended or adjusted under 35 U.S.C. 154(b) by 0 days.

(21) Appl. No.: 12/867,997

(22) PCT Filed: Feb. 18, 2009

(86) PCT No.: PCT/US2009/001071
§ 371 (c)(1),
(2), (4) Date: Nov. 30, 2010

(87) PCT Pub. No.: WO2009/105238
PCT Pub. Date: Aug. 27, 2009

(65) Prior Publication Data
US 2011/0065664 A1 Mar. 17, 2011

Related U.S. Application Data

(60) Provisional application No. 61/066,192, filed on Feb. 18, 2008, provisional application No. 61/068,903, filed on Mar. 11, 2008.

(51) Int. Cl.
*A01N 33/02* (2006.01)
*A61K 31/135* (2006.01)

(52) U.S. Cl. ...................................... 514/646

(58) Field of Classification Search .................. None
See application file for complete search history.

(56) References Cited

OTHER PUBLICATIONS

Saegusa etal. Preparation and characterization of fluorine-containing aromatic condensation polymers.*

Heinemann et al. Gemcitabine and cisplatin in the treatment of advanced or metastatic pancreatic cancer. Annals of Oncology, 11: 1399-1403, 2000.*
Hatakeyama et al. Anti-cancer activity of NVP-TAE226, a potent dual FAK/IGF-IR kinase inhibitor, against pancreatic carcinoma. Journal of Clinical Oncology, 2006 ASCO Annaul Meeting Proceedings Part I. vol. 24, No. 18S (Jun. 20 Supplement). Abstract 13162.*
Ji Johnson et al. Relationships between drug activity in NCI preclinical in vitro and in vov models and early clinical trials. British Journal of CAncer, 2001, 9 sheets.*
S.N. Hochwald et al., "A novel small molecule inhibitor of FAK decreases growth of human pancreatic cancer", Cell Cycle, 8(15), pp. 2435-2443 (2009).
V.M. Golubovskaya et al., "A Small Molecule Inhibitor, 1,2,4,5-Benzenetetraamine Tetrahydrochloride, Targeting the Y397 Site of Focal Adhesion Kinase Decreases Tumor Growth", J. Med. Chem., vol. 51, pp. 7405-7416 (2008).
A.S. Strimpakos et al., "Pancreatic Cancer: Translating Lessons from Mouse Models", Journal of the Pancreas, 10(2), pp. 98-103 (2009).
C.H. Liao et al., "Garcinol Modulates Tyrosine Phosphorylation of FAK and Subsequently Induces Apoptosis Through Down-Regulation of Src, ERK, and Akt Survival Signaling in Human Colon Cancer Cells", Journal of Cellular Biochemistry, 96(155), pp. 155-169 (2005).

* cited by examiner

*Primary Examiner* — Brandon Fetterolf
*Assistant Examiner* — Anna Pagonakis
(74) *Attorney, Agent, or Firm* — Edwards Wildman Palmer LLP; Jeffrey D. Hsi; Elizabeth Spar

(57) ABSTRACT

The invention relates to phosphorylation inhibitor compounds and methods of identifying and using them. The invention further relates to pharmaceutical compositions and methods for treating cell proliferative disorders, especially cancer.

14 Claims, 17 Drawing Sheets

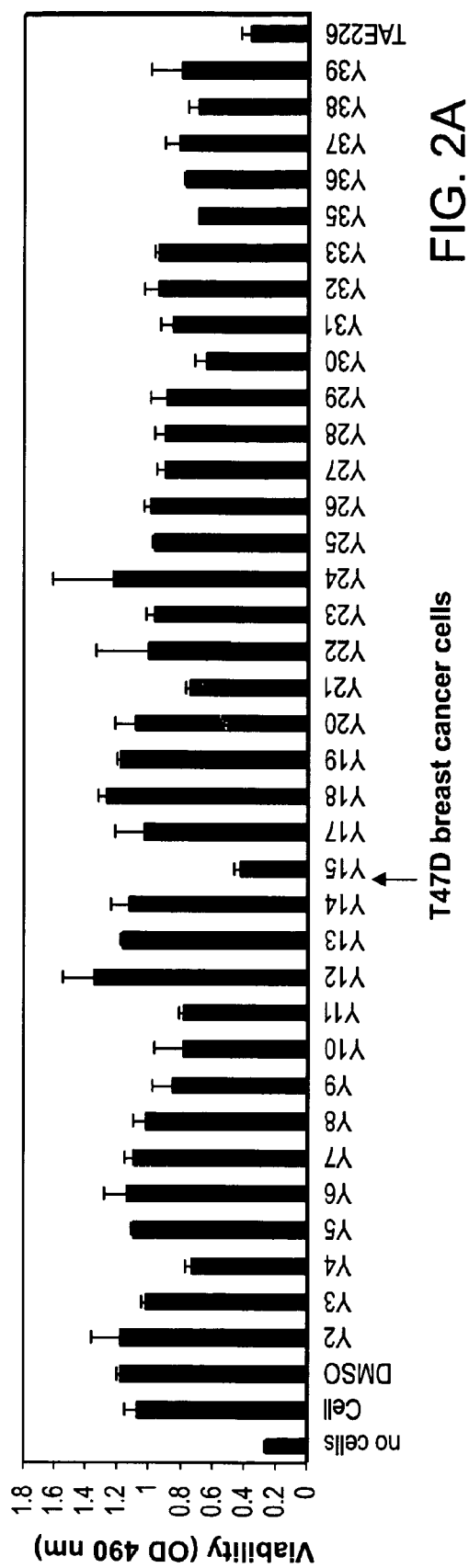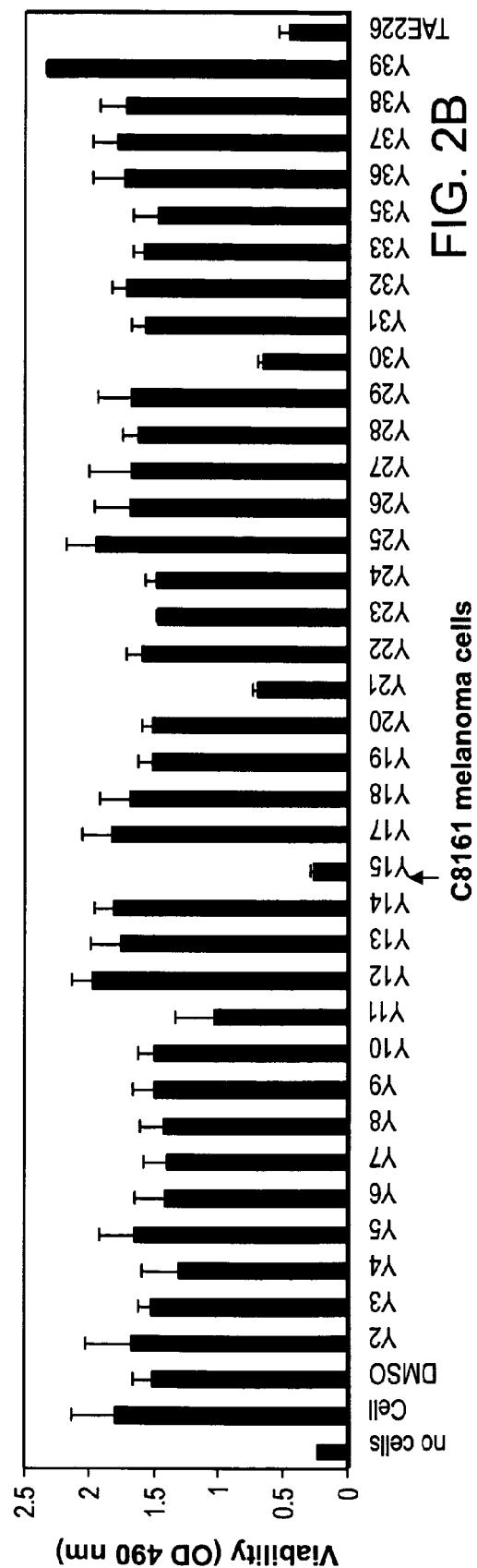

benzene-1,2,4,5-tetraamine
tetrahydrocloride
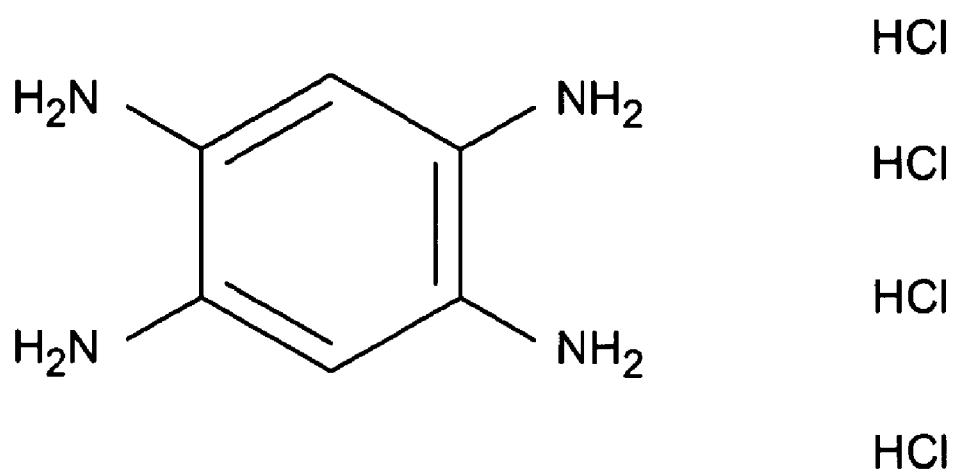
FIG. 3

BT474 cells
Hoechst staining
Untreated
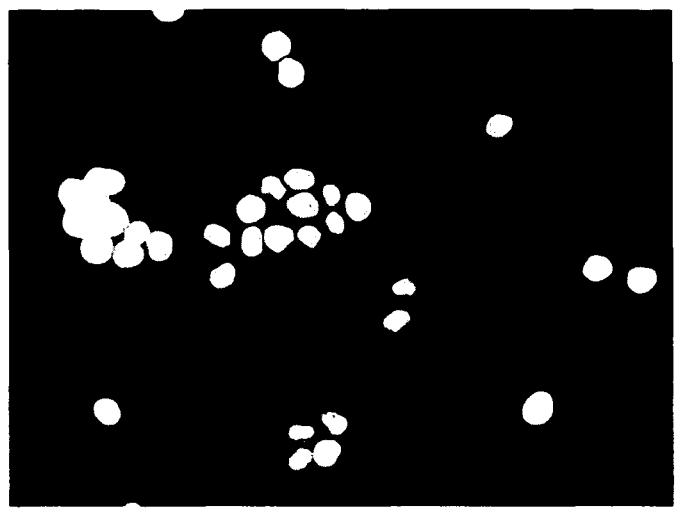
Y15 200 µM
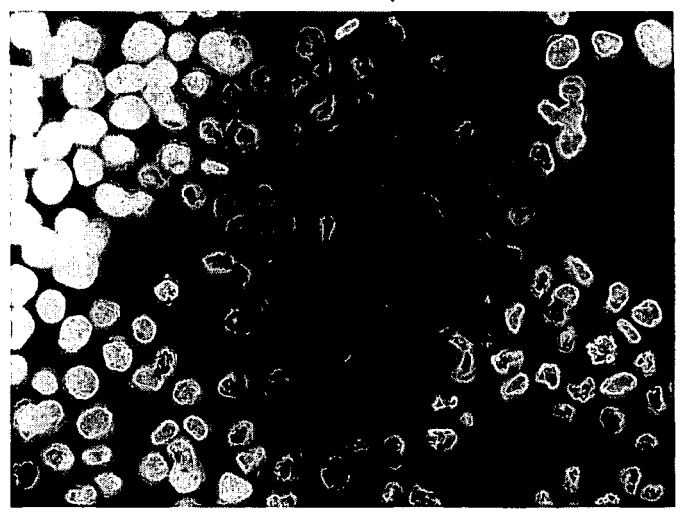
TAE-226 20 µM
FIG. 6C

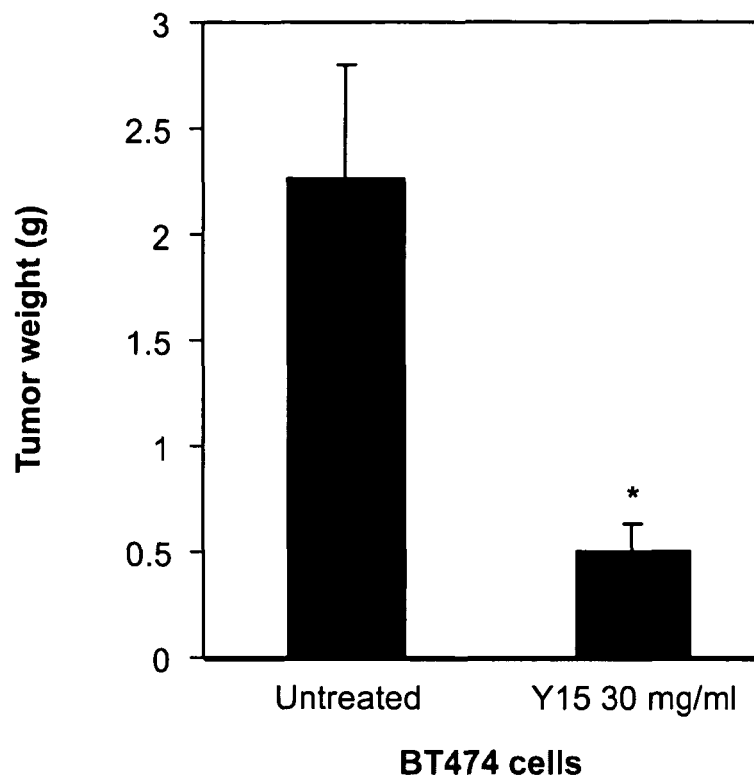
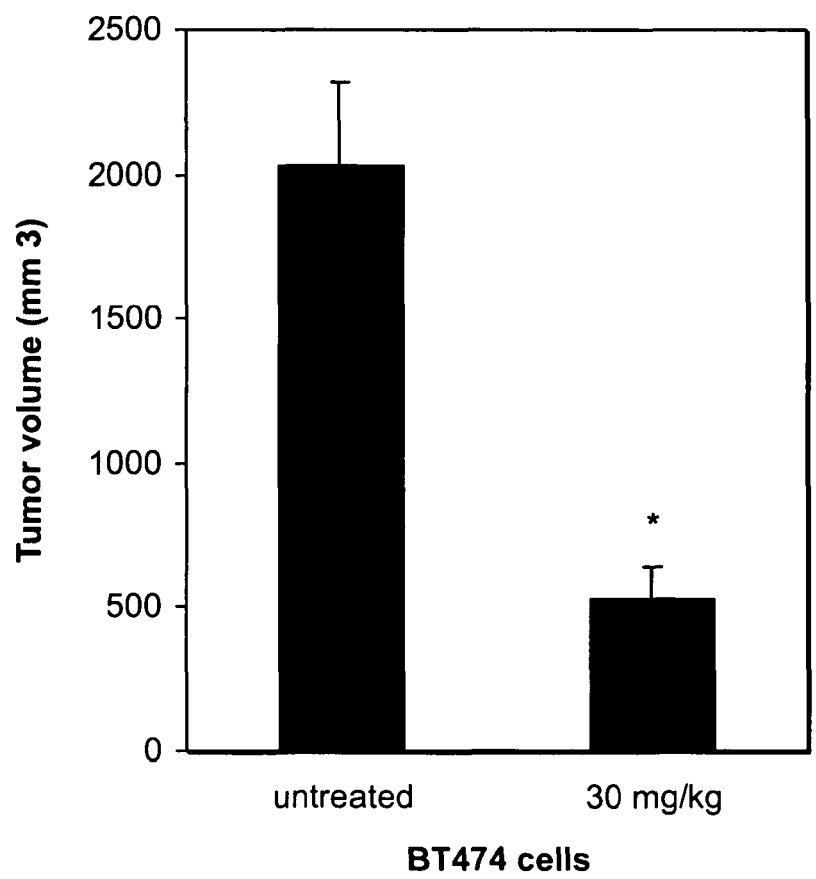
FIG. 7B

KINASE PROTEIN BINDING INHIBITORS

CROSS-REFERENCE TO RELATED APPLICATIONS

This application is the U.S. national phase application, pursuant to 35 U.S.C. §371, of PCT International Application No. PCT/US2009/001071, filed Feb. 18, 2009, which claims the benefit of U.S. Provisional Patent Applications No. 61/066,192, filed Feb. 18, 2008 and 61/068,903, filed Mar. 11, 2008, the contents of which are incorporated herein by reference in their entirety.

STATEMENT OF RIGHTS TO INVENTIONS MADE UNDER FEDERALLY SPONSORED RESEARCH

This work was supported in part by a National Institutes of Health/NCI Grant, Grant No. 2-R01-CA65910-09-13. The government has certain rights in the invention.

BACKGROUND OF THE INVENTION

Focal Adhesion Kinase (FAK) is an important survival molecule that is upregulated in a broad range of solid tumors and is expressed at very low levels in normal tissues, creating a therapeutic window and making this protein a highly attractive target for the treatment of cancer See, e.g., WO 2005/049852, the contents of which are incorporated by reference.

The market for novel drug therapy targeting cancers of the breast, colon, pancreas, and thyroid is extensive. According to the American Cancer Society, it is estimated that 425,000 new cases of these cancers will be diagnosed this year in this country alone. Cancer drug therapy is an existing major product line of several pharmaceutical companies, and the development of drugs targeting FAK would be a natural complement to their existing products.

FAK is overexpressed in many cancer types compared to other kinase targets. Compounds that target FAK could be prescribed for many cancer types including breast, colon, pancreas, thyroid, lung, and melanoma.

Several groups are exploring the targeting of FAK as potential cancer therapeutics. The targeting of FAK typically has been focused on the kinase domain of FAK. This approach has proven unsuccessful as disruption of the kinase domain does not specifically interfere with the signaling downstream of FAK and other related tyrosine kinases have been affected by the drugs. Delineated herein is a novel approach that focuses on FAK phosphorylation.

FAK is a 125 kDa protein that localizes to focal adhesions (1) and is activated and tyrosine phosphorylated in response to integrin clustering (2). Tyrosine 397 is an autophosphorylation site of FAK and is a critical component in downstream signaling (3), providing a high-affinity binding site for the SH2 domain of Src family kinases (4), (5). The interaction between Y397-activated FAK and Src leads to a cascade of tyrosine phosphorylation of multiple sites in FAK (-576, -577, -925), as well as other signaling molecules such as p130$^{CAS}$ and paxillin, resulting in cytoskeletal changes and activation of other downstream signaling pathways (6). Y397 is also a site of binding PI3 kinase, growth factor receptor binding Grb-7, Shc, and other proteins. Thus, the Y397 site is one of the main phosphorylation sites that activate FAK signaling in the cells.

Focal adhesion kinase is involved in multiple cellular functions such as cell proliferation, survival, motility, invasion, metastasis, and angiogenesis (7). Different approaches to inhibit FAK with FAK anti-sense oligonucleotides (8), dominant-negative C-terminal domain of FAK, FAK-CD or FRNK (9,10) or FAK siRNA (11), (12) caused decreased cellular viability, growth inhibition or apoptosis. Recently, FAK has been proposed to be a new potential therapeutic target in cancer (13,14). Two novel kinase inhibitors of FAK, blocking FAK catalytic activity, were developed and reported recently, one by Novartis: NVP-TAE226 (15) (16) and another by Pfizer: PF-573,228 (17). The first inhibitor, TAE226, inhibited glioma and ovarian tumor growth in vivo (16,18), although it also inhibited IGFR kinase (16). The efficacy of the PF-573,228 on tumor growth in vivo has not been reported, it inhibited only motility and did not inhibit cell growth and survival in vitro (17). Both of these inhibitors effectively blocked Y397-FAK phosphorylation.

Since the Y397 site is important for FAK survival function, we performed a computer modeling approach, described in (19), to specifically target the Y397-site of FAK and to find potential small-molecule drugs that inhibit FAK function and decrease cell viability and tumor growth.

We found that certain compounds, including 1,2,4,5-benzenetetraamine tetrahydrochloride, called Y15, targets the Y397 site, directly and specifically decreases Y397-phosphorylation of FAK in vitro, inhibits cancer cell viability in vitro, causes detachment, decreases cell adhesion and blocks tumor growth in vivo. Thus, targeting the Y397 site can be an effective therapy approach for developing future novel FAK inhibitors.

SUMMARY OF THE INVENTION

In one aspect, the invention provides a method of treating a subject suffering from or susceptible to a cell proliferative disorder comprising administering to subject in need thereof a therapeutically effective amount of a compound capable of modulating FAK protein-protein binding interactions. In one embodiment, the compound is capable of binding to or interacting with a binding pocket that affects FAK binding. In another embodiment, the compound is capable of binding to or interacting with a binding pocket that affects FAK phosphorylation.

In one embodiment, the compound is capable of inhibiting Y397 phosphorylation of FAK. In one embodiment, the compound is identified as capable of inhibiting Y397 phosphorylation of FAK.

In one aspect, the invention provides a method of treating a subject suffering from or susceptible to a cell proliferative disorder. The method includes administering to a subject in need thereof a therapeutically effective amount of a FAK phosphorylation inhibitor compound.

In another aspect, the invention provides a method of treating a subject suffering from or susceptible to a cell proliferative disorder. The method includes administering to a subject in need thereof a therapeutically effective amount of a compound capable of inhibiting Y397 of FAK.

In another embodiment, the invention provides a method of treating a subject suffering from or susceptible to a cell proliferative disorder. The method includes administering to a subject identified as in need thereof a therapeutically effective amount of a FAK phosphorylation inhibitor compound or a FAK Y397 phosphorylation inhibitor compound.

In another aspect, the invention provides a method of treating a subject suffering from or susceptible to a cell proliferative disorder, including cancer. The method includes administering to a subject in need thereof a therapeutically effective amount of a compound capable of binding to a Y397 domain of FAK.

In another aspect, the invention provides a method of treating a subject suffering from or susceptible to cancer, comprising administering to the subject an effective amount of a compound capable of disrupting FAK binding (including with FAK-binding partners), such that the subject is treated.

In another aspect, the invention provides a method of treating a subject suffering from or susceptible to cancer, comprising administering to the subject an effective amount of a compound capable of binding to a Y397 domain of FAK, such that the subject is treated.

In another aspect, the compound has an inhibiting effect on FAK autophosphorylation at least 2 times greater (e.g., "X" times greater, where X is a number between 2 and 1000, inclusive) than its inhibiting effect (e.g., binding) on other kinases; including wherein the other kinase is IGFR-1, MAPK, or AKT; or c-RAF, c-Src, EGFR, VEGFR-3, IGF-1, Met, PDGFR-$\alpha$, Pyk2, PI3K (p110$\delta$/p85$\alpha$), and the like.

In another aspect, the invention provides a method of inhibiting cell adhesion, comprising contacting a compound identified herein with a cell such that cell adhesion is inhibited. In another aspect, the invention provides a method of inhibiting cell adhesion in a subject, comprising administering to the subject an effective amount of a compound capable of binding to (or identified as capable of binding to) a Y397 domain of FAK.

In another aspect, the invention provides a method for identifying a compound that modulates FAK protein-protein binding interaction, the method comprising obtaining a crystal structure of a FAK protein or obtaining information relating to the crystal structure of a FAK protein, and modeling a test compound into or on the FAK protein structure to determine whether the compound modulates the interaction of a FAK protein-protein binding or modulates phosphorylation of FAK (e.g., at Y397). In certain embodiments, the step of modeling comprises modeling or determining the ability of the compound to bind to or associate with a binding pocket defined by structure coordinates of the Y397 domain of FAK.

Yet another aspect of the invention is a method for identifying a compound that inhibits cell proliferation. The method includes contacting a FAK complex with a test compound, and evaluating the ability of the test compound to modulate (e.g., inhibit), the phosphorylation of (e.g., at Y397) of FAK, inhibit cell proliferation, induce apoptosis, or modulate FAK binding with a FAK protein binding partner.

Yet another aspect of the invention is a method for identifying a compound that modulates the activity of FAK, the method comprising using the atomic coordinates of the Y397 domain of FAK, to generate a three-dimensional structure (e.g., in silico) of a molecule comprising a binding pocket, and employing the three-dimensional structure to identify a compound that modulates the activity (e.g., phosphorylation) of the Y397 domain of FAK or modulate FAK binding with a FAK protein binding partner.

In another aspect, the invention provides a packaged composition including a therapeutically effective amount of a FAK phosphorylation inhibitor or FAK protein-protein binding interaction inhibitor compound and a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In one aspect, the invention provides a kit for treating a cell proliferative disorder in a subject is provided and includes a compound herein, a pharmaceutically acceptable esters, salts, and prodrugs thereof, and instructions for use. In further aspects, the invention provides kits for inhibiting cell proliferation, assessing the efficacy of an anti-cell proliferative treatment in a subject, monitoring the progress of a subject being treated with a cell proliferation inhibitor, selecting a subject with a cell proliferative disorder for treatment with cell proliferation inhibitor, and/or treating a subject suffering from or susceptible to cancer. In certain embodiments, the invention provides: a kit for treating a cell proliferative disorder in a subject, the kit comprising a compound capable of modulating (e.g., inhibiting) FAK activity (e.g., phosphorylation) or FAK protein-protein binding interactions.

In another aspect, the invention relates to a three-dimensional structure of a Y397 domain of FAK, or a FAK protein binding partner, each alone or combinations thereof.

Thus, the present invention provides molecules or molecular complexes that comprise either one or both of these binding pockets or homologues of either binding pocket that have similar three-dimensional shapes.

The invention also provides a pharmaceutical compositions of the compounds described herein, comprising a compound capable of inhibiting Y397 phosphorylation of FAK or modulating FAK binding with a FAK protein binding partner, or a pharmaceutically acceptable ester, salt, or prodrug thereof, together with a pharmaceutically acceptable carrier.

In another aspect, the invention provides a machine readable storage medium which comprises the structural coordinates of a binding pocket defining the Y397 domain of FAK, or a homologous binding pocket.

In another aspect, the invention provides a computer for producing a three-dimensional representation of a molecule or molecular complex, wherein said molecule or molecular complex comprises a binding pocket defined by structure coordinates of the Y397 domain of FAK; or b) a three-dimensional representation of a homologue of said molecule or molecular complex, wherein said homologue comprises a binding pocket that has a root mean square deviation from the backbone atoms of said amino acids of not more than about 2.0 angstroms. The computer includes: (i) a machine-readable data storage medium comprising a data storage material encoded with machine-readable data, wherein said data comprises the structure coordinates of the Y397 domain of FAK; (ii) a working memory for storing instructions for processing said machine-readable data; (iii) a central-processing unit coupled to said working memory and to said machine-readable data storage medium for processing said machine readable data into said three-dimensional representation; and (iv) a display coupled to said central-processing unit for displaying said three-dimensional representation.

The invention also provides methods for designing, evaluating and identifying compounds which bind to the aforementioned binding pockets. Other embodiments of the invention are disclosed infra.

BRIEF DESCRIPTION OF THE DRAWINGS

The present invention is further described below with reference to the following non-limiting examples and with reference to the following figures, in which:

FIG. 2. FIGS. 2A, B illustrate the effect of compounds targeting Y397 site on viability of breast cancer and melanoma cell lines.

FIG. 3. FIG. 3. illustrates the structure of 1,2,4,5-benzenetetraamine tetrahydrochloride (Y15) compound.

FIG. 5. illustrates that Y15 directly blocks in vitro kinase activity of FAK.

FIG. 6. FIG. 6C illustrates Hoechst staining of Y15-treated BT474 cells.

FIG. 10 illustrates the effect of Y15 on cell viability in pancreatic cancer cells and tumor associated fibroblasts.

DETAILED DESCRIPTION OF THE INVENTION

Figure 1B:
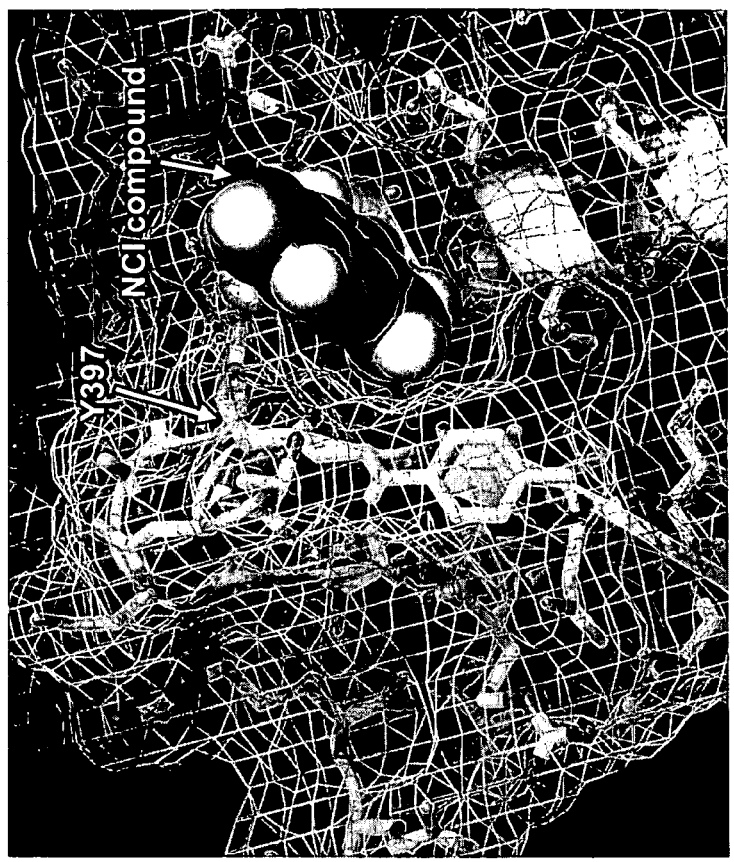
FIG. 1.
FIGS. 1A, B illustrate targeting of Y397 site of FAK by structure-based molecular docking approach.

The present inventors have now discovered a therapeutic strategy that addresses inhibition of FAK phosphorylation by targeting FAK Y397 phosphorylation. Such interactions are relevant for modulation of apoptosis and cell proliferation, particularly in certain cancer types where FAK mechanisms play a significant role.

The present invention relates, at least in part, to the discovery that the FAK Y397 phosphorylation mediated processes are useful as targets (e.g., selective) for tumor therapy. Disruption of these interactions cause loss of viability and apoptosis in cancer but not in normal cells in vitro.

1. Definitions

Before further description of the present invention, and in order that the invention may be more readily understood, certain terms are first defined and collected here for convenience.

The term "administration" or "administering" includes routes of introducing the compound of the invention(s) to a subject to perform their intended function. Examples of routes of administration that may be used include injection (subcutaneous, intravenous, parenterally, intraperitoneally, intrathecal), oral, inhalation, rectal and transdermal. The pharmaceutical preparations may be given by forms suitable for each administration route. For example, these preparations are administered in tablets or capsule form, by injection, inhalation, eye lotion, ointment, suppository, etc. administration by injection, infusion or inhalation; topical by lotion or ointment; and rectal by suppositories. Oral administration is preferred. The injection can be bolus or can be continuous infusion. Depending on the route of administration, the compound of the invention can be coated with or disposed in a selected material to protect it from natural conditions which may detrimentally effect its ability to perform its intended function. The compound of the invention can be administered alone, or in conjunction with either another agent as described above or with a pharmaceutically-acceptable carrier, or both. The compound of the invention can be administered prior to the administration of the other agent, simultaneously with the agent, or after the administration of the agent. Furthermore, the compound of the invention can also be administered in a pro-drug form which is converted into its active metabolite, or more active metabolite in vivo.

The term "alkyl" refers to the radical of saturated aliphatic groups, including straight-chain alkyl groups, branched-chain alkyl groups, cycloalkyl(alicyclic) groups, alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., C1-C30 for straight chain, $C_3$-$C_{30}$ for branched chain), preferably 26 or fewer, and more preferably 20 or fewer, and still more preferably 4 or fewer. Likewise, preferred cycloalkyls have from 3-10 carbon atoms in their ring structure, and more preferably have 3, 4, 5, 6 or 7 carbons in the ring structure.

Moreover, the term alkyl as used throughout the specification and sentences is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate. Cycloalkyls can be further substituted, e.g., with the substituents described above. An "alkylaryl" moiety is an alkyl substituted with an aryl (e.g., phenylmethyl(benzyl)). The term "alkyl" also includes unsaturated aliphatic groups analogous in length and possible substitution to the alkyls described above, but that contain at least one double or triple bond respectively.

Unless the number of carbons is otherwise specified, "lower alkyl" as used herein means an alkyl group, as defined above, but having from one to ten carbons, more preferably from one to six, and still more preferably from one to four carbon atoms in its backbone structure, which may be straight or branched-chain. Examples of lower alkyl groups include methyl, ethyl, n-propyl, i-propyl, tert-butyl, hexyl, heptyl, octyl and so forth. In preferred embodiment, the term "lower alkyl" includes a straight chain alkyl having 4 or fewer carbon atoms in its backbone, e.g., C1-C4 alkyl.

The terms "alkoxyalkyl," "polyaminoalkyl" and "thioalkoxyalkyl" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aryl" as used herein, refers to the radical of aryl groups, including 5- and 6-membered single-ring aromatic groups that may include from zero to four heteroatoms, for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like. Those aryl groups having heteroatoms in the ring structure may also be referred to as "aryl heterocycles," "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "associating with" refers to a condition of proximity between a chemical entity or compound, or portions thereof, and a binding pocket or binding site on a protein. The association may be non-covalent (wherein the juxtaposition is energetically favored by hydrogen bonding or van der Waals or electrostatic interactions) or it may be covalent.

The term "binding pocket", as used herein, refers to a region of a molecule or molecular complex, that, as a result of its shape, favorably associates with another chemical entity or compound.

The language "biological activities" of a compound of the invention includes all activities elicited by compound of the inventions in a responsive cell. It includes genomic and non-genomic activities elicited by these compounds.

"Biological composition" or "biological sample" refers to a composition containing or derived from cells or biopolymers. Cell-containing compositions include, for example, mammalian blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, saliva, placental extracts, a cryoprecipitate, a cryosupernatant, a cell lysate, mammalian cell culture or culture medium, products of fermentation, ascites fluid, proteins induced in blood cells, and products produced in cell culture by normal or transformed cells (e.g., via recombinant DNA or monoclonal antibody technology). Biological compositions can be cell-free. In a preferred embodiment, a suitable biological composition or biological sample is a red blood cell suspension. In some embodiments, the blood cell suspension includes mammalian blood cells. Preferably, the blood cells are obtained from a human, a non-human primate, a dog, a cat, a horse, a cow, a goat, a sheep or a pig. In preferred embodiments, the blood cell suspension includes red blood cells and/or platelets and/or leukocytes and/or bone marrow cells.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "effective amount" includes an amount effective, at dosages and for periods of time necessary, to achieve the desired result, e.g., sufficient to treat a cell proliferative disorder. An effective amount of compound of the invention may vary according to factors such as the disease state, age, and weight of the subject, and the ability of the compound of the invention to elicit a desired response in the subject. Dosage regimens may be adjusted to provide the optimum therapeutic response. An effective amount is also one in which any toxic or detrimental effects (e.g., side effects) of the compound of the invention are outweighed by the therapeutically beneficial effects.

A therapeutically effective amount of compound of the invention (i.e., an effective dosage) may range from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of a compound of the invention can include a single treatment or, preferably, can include a series of treatments. In one example, a subject is treated with a compound of the invention in the range of between about 0.1 to 20 mg/kg body weight, one time per week for between about 1 to 10 weeks, preferably between 2 to 8 weeks, more preferably between about 3 to 7 weeks, and even more preferably for about 4, 5, or 6 weeks. It will also be appreciated that the effective dosage of a compound of the invention used for treatment may increase or decrease over the course of a particular treatment.

The term "enantiomers" refers to two stereoisomers of a compound which are non-superimposable mirror images of one another. An equimolar mixture of two enantiomers is called a "racemic mixture" or a "racemate." The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein. All such isomeric forms of such compounds are expressly included in the present invention. All crystal forms of the compounds described herein are expressly included in the present invention.

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "homeostasis" is art-recognized to mean maintenance of static, or constant, conditions in an internal environment.

The language "improved biological properties" refers to any activity inherent in a compound of the invention that enhances its effectiveness in vivo. In a preferred embodiment, this term refers to any qualitative or quantitative improved therapeutic property of a compound of the invention, such as reduced toxicity.

The term "cell proliferative disorder" includes disorders involving the undesired or uncontrolled proliferation of a cell.

Examples of such disorders include, but are not limited to, tumors or cancers (e.g., lung (small cell and non-small cell), thyroid, prostate, pancreatic, breast or colon), sarcoma or melanoma.

The language "a FAK protein-protein binding partner" refers to a protein (including those delineated herein) that bind with FAK (e.g., full length, N-terminus, C-terminus, carboxy terminus, kinase domain, FERM domain, FAT domain).

The term "optionally substituted" is intended to encompass groups that are unsubstituted or are substituted by other than hydrogen at one or more available positions, typically 1, 2, 3, 4 or 5 positions, by one or more suitable groups (which may be the same or different). Such optional substituents include, for example, hydroxy, halogen, cyano, nitro, $C_1$-$C_8$alkyl, $C_2$-$C_8$ alkenyl, $C_2$-$C_8$alkynyl, $C_1$-$C_8$alkoxy, $C_2$-$C_8$alkyl ether, $C_3$-$C_8$alkanone, $C_1$-$C_8$alkylthio, amino, mono- or di-(C1-$C_8$alkyl)amino, halo$C_1$-$C_8$alkyl, halo$C_1$-$C_8$alkoxy, $C_1$-$C_8$alkanoyl, $C_2$-$C_8$alkanoyloxy, $C_1$-$C_8$alkoxycarbonyl, —COOH, —CONH$_2$, mono- or di-($C_1$-$C_8$alkyl)aminocarbonyl, —SO$_2$NH$_2$, and/or mono or di($C_1$-$C_8$alkyl)sulfonamido, as well as carbocyclic and heterocyclic groups. Optional substitution is also indicated by the phrase "substituted with from 0 to X substituents," where X is the maximum number of possible substituents. Certain optionally substituted groups are substituted with from 0 to 2, 3 or 4 independently selected substituents (i.e., are unsubstituted or substituted with up to the recited maximum number of substituents).

The term "isomers" or "stereoisomers" refers to compounds which have identical chemical constitution, but differ with regard to the arrangement of the atoms or groups in space.

The term "modulate" refers to an increase or decrease, e.g., in the ability of a cell to proliferate in response to exposure to a compound of the invention, e.g., the inhibition of proliferation of at least a sub-population of cells in an animal such that a desired end result is achieved, e.g., a therapeutic result.

The term "obtaining" as in "obtaining a compound capable of inhibiting Y397 phosphorylation of FAK" is intended to include purchasing, synthesizing or otherwise acquiring the compound.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The terms "polycyclyl" or "polycyclic radical" refer to the radical of two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "prodrug" or "pro-drug" includes compounds with moieties that can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkylamino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

The language "a prophylactically effective amount" of a compound refers to an amount of a compound of the invention any formula herein or otherwise described herein which is effective, upon single or multiple dose administration to the patient, in preventing or treating a cell proliferative disorder.

The language "reduced toxicity" is intended to include a reduction in any undesired side effect elicited by a compound of the invention when administered in vivo.

The term "sulfhydryl" or "thiol" means —SH.

The term "subject" includes organisms which are capable of suffering from a cell proliferative disorder or who could otherwise benefit from the administration of a compound of the invention of the invention, such as human and non-human animals. Preferred humans include human patients suffering from or prone to suffering from a cell proliferative disorder or associated state, as described herein. The term "non-human animals" of the invention includes all vertebrates, e.g., mammals, e.g., rodents, e.g., mice, and non-mammals, such as non-human primates, e.g., sheep, dog, cow, chickens, amphibians, reptiles, etc.

The term "susceptible to a cell proliferative disorder" is meant to include subjects at risk of developing disorder of cell proliferation, e.g., cancer, i.e., subjects suffering from viral infection with cancer viruses, subjects that have been exposed to ionizing radiation or carcinogenic compounds, subjects having a family or medical history of cancer, and the like.

The phrases "systemic administration," "administered systemically", "peripheral administration" and "administered peripherally" as used herein mean the administration of a compound of the invention(s), drug or other material, such that it enters the patient's system and, thus, is subject to metabolism and other like processes, for example, subcutaneous administration.

The language "therapeutically effective amount" of a compound of the invention of the invention refers to an amount of an agent which is effective, upon single or multiple dose administration to the patient, in inhibiting cell proliferation and/or symptoms of a cell proliferative disorder, or in prolonging the survivability of the patient with such a cell proliferative disorder beyond that expected in the absence of such treatment.

With respect to the nomenclature of a chiral center, terms "d" and "l" configuration are as defined by the IUPAC Recommendations. As to the use of the terms, diastereomer, racemate, epimer and enantiomer will be used in their normal context to describe the stereochemistry of preparations.

2. Compounds of the Invention

In one aspect, the invention provides compounds capable of modulating (e.g., inhibiting or stimulating) (directly or indirectly) FAK binding activity.

In one embodiment, the invention provides a compound capable of modulating FAK protein-protein binding; and pharmaceutically acceptable esters, salts, and prodrugs thereof.

Certain preferred compounds include compounds specifically delineated herein:

Inhibitor:
Y11: 3,5,7-triaza-1-azoniatricyclo(3.3.1.13,7)decane, 1-(2-hydroxyethyl)-, bromide;
Y15: 1,2,4,5-benzenetetraamine tetrahydrochloride;
Y30: 9-thia-1,3,6,8-tetraazatricyclo[4.3.1.1(3,8)]undecane, 9,9-dioxide;

The invention also relates to the pharmaceutically acceptable salts and esters of the above-mentioned compounds.

Naturally occurring or synthetic isomers can be separated in several ways known in the art. Methods for separating a racemic mixture of two enantiomers include chromatography using a chiral stationary phase (see, e.g., "Chiral Liquid Chromatography," W. J. Lough, Ed. Chapman and Hall, New York (1989)). Enantiomers can also be separated by classical resolution techniques. For example, formation of diastereomeric salts and fractional crystallization can be used to separate enantiomers. For the separation of enantiomers of carboxylic acids, the diastereomeric salts can be formed by addition of enantiomerically pure chiral bases such as brucine, quinine, ephedrine, strychnine, and the like. Alternatively, diastereomeric esters can be formed with enantiomerically pure chiral alcohols such as menthol, followed by separation of the diastereomeric esters and hydrolysis to yield the free, enantiomerically enriched carboxylic acid. For separation of the optical isomers of amino compounds, addition of chiral carboxylic or sulfonic acids, such as camphorsulfonic acid, tartaric acid, mandelic acid, or lactic acid can result in formation of the diastereomeric salts.

According to another embodiment, the invention provides compounds capable of inhibiting Y397 phosphorylation of FAK produced or identified by the methods described herein.

3. Uses of the Compounds of the Invention

In one embodiment, the invention provides methods for treating a subject for a cell proliferative disorder, by administering to the subject an effective amount of a compound capable of inhibiting Y397 phosphorylation of FAK. A cell proliferative disorder includes cancer. In certain embodiments, the subject is a mammal, e.g., a primate, e.g., a human.

In this embodiment, the compounds of the invention may either directly or indirectly modulate the phosphorylation activity of FAK, or specific domains thereof. A cell undergoing uncontrolled proliferation can be contacted with a compound of the invention to inhibit cell proliferation or induce apoptosis. Contacting cells or administering the compounds of the invention to a subject is one method of treating a cell or a subject suffering from or susceptible to unwanted or undesired cell proliferation or a cell proliferative disorder.

In one embodiment, a method of treating a subject suffering from or susceptible to unwanted or undesired cell proliferation or a cell proliferative disorder includes administering to a subject in need thereof a therapeutically effective amount of a compound capable of inhibiting phosphorylation of FAK or domains thereof, to thereby treat the subject suffering from or susceptible to unwanted or undesired cell proliferation or a cell proliferative disorder. Exemplary compounds include compounds described herein.

Thus, in one embodiment, the invention provides methods for treating a subject for a cell proliferative disorder, by administering to the subject an effective amount of a compound capable of inhibiting Y397 phosphorylation of FAK.

In certain embodiments, the methods of the invention include administering to a subject a therapeutically effective amount of a compound of the invention in combination with another pharmaceutically active compound. Examples of pharmaceutically active compounds include compounds known to treat cell proliferative disorders, e.g., anticancer agent, antiproliferative agent, chemotherapeutic. Other pharmaceutically active compounds that may be used can be found in *Harrison's Principles of Internal Medicine*, Thirteenth Edition, Eds. T. R. Harrison et al. McGraw-Hill N.Y., NY; and the Physicians Desk Reference 50th Edition 1997, Oradell N.J., Medical Economics Co., the complete contents of which are expressly incorporated herein by reference. The compound of the invention and the pharmaceutically active compound may be administered to the subject in the same pharmaceutical composition or in different pharmaceutical compositions (at the same time or at different times).

In certain embodiments, the compound of the invention can be used in combination therapy with conventional cancer chemotherapeutics. Conventional treatment regimens for leukemia and for other tumors include radiation, drugs, or a combination of both. In addition to radiation, the following drugs, usually in combinations with each other, are often used to treat acute leukemias: vincristine, prednisone, methotrexate, mercaptopurine, cyclophosphamide, and cytarabine. Other examples include, for example, doxorubicin, cisplatin, taxol, 5-fluorouracil, etoposid, gemcitabine, etc., which demonstrate advantages (e.g., chemosensitization of cells) in combination with the compounds described herein. In chronic leukemia, for example, busulfan, melphalan, and chlorambucil can be used in combination. Most conventional anti-cancer drugs are highly toxic and tend to make patients quite ill while undergoing treatment. Vigorous therapy is based on the premise that unless every cancerous cell is destroyed, the residual cells will multiply and cause a relapse.

Methods delineated herein include those wherein the subject is identified as in need of a particular stated treatment. Identifying a subject in need of such treatment can be in the judgment of a subject or a health care professional and can be subjective (e.g. opinion) or objective (e.g. measurable by a test or diagnostic method). In other methods, the subject is prescreened or identified as in need of such treatment by assessment for a relevant marker or indicator of suitability for such treatment.

Determination of a therapeutically effective anti-proliferative amount or a prophylactically effective anti-proliferative amount of the compound of the invention of the invention, can be readily made by the physician or veterinarian (the "attending clinician"), as one skilled in the art, by the use of known techniques and by observing results obtained under analogous circumstances. The dosages may be varied depending upon the requirements of the patient in the judgment of the attending clinician; the severity of the condition being treated and the particular compound being employed. In determining the therapeutically effective anti-proliferative amount or dose, and the prophylactically effective anti-proliferative amount or dose, a number of factors are considered by the attending clinician, including, but not limited to: the specific cell proliferative disorder involved; pharmacodynamic characteristics of the particular agent and its mode and route of administration; the desired time course of treatment; the species of mammal; its size, age, and general health; the specific disease involved; the degree of or involvement or the severity of the disease; the response of the individual patient; the particular compound administered; the mode of administration; the bioavailability characteristics of the preparation administered; the dose regimen selected; the kind of concurrent treatment (i.e., the interaction of the compound of the invention with other co-administered therapeutics); and other relevant circumstances.

Treatment can be initiated with smaller dosages, which are less than the optimum dose of the compound. Thereafter, the dosage may be increased by small increments until the optimum effect under the circumstances is reached. For convenience, the total daily dosage may be divided and administered in portions during the day if desired. A therapeutically effective amount and a prophylactically effective anti-proliferative amount of a compound of the invention of the invention is expected to vary from about 0.1 milligram per kilogram of body weight per day (mg/kg/day) to about 100 mg/kg/day.

Compounds determined to be effective for the prevention or treatment of cell proliferative disorders in animals, e.g., dogs, chickens, and rodents, may also be useful in treatment of tumors in humans. Those skilled in the art of treating tumors in humans will know, based upon the data obtained in animal studies, the dosage and route of administration of the compound to humans. In general, the dosage and route of administration in humans is expected to be similar to that in animals.

The identification of those patients who are in need of prophylactic treatment for cell proliferative disorders is well within the ability and knowledge of one skilled in the art. Certain of the methods for identification of patients which are at risk of developing cell proliferative disorders which can be treated by the subject method are appreciated in the medical arts, such as family history, and the presence of risk factors associated with the development of that disease state in the subject patient. A clinician skilled in the art can readily identify such candidate patients, by the use of, for example, clinical tests, physical examination and medical/family history.

A method of assessing the efficacy of a treatment in a subject includes determining the pre-treatment extent of a cell proliferative disorder by methods well known in the art (e.g., determining tumor size or screening for tumor markers where the cell proliferative disorder is cancer) and then administering a therapeutically effective amount of an inhibitor of cell proliferation (e.g., those described herein) according to the invention to the subject. After an appropriate period of time after the administration of the compound (e.g., 1 day, 1 week, 2 weeks, one month, six months), the extent of the cell proliferative disorder is determined again. The modulation (e.g., decrease) of the extent or invasiveness of the cell proliferative disorder indicates efficacy of the treatment. The extent or invasiveness of the cell proliferative disorder may be determined periodically throughout treatment. For example, the extent or invasiveness of the cell proliferative disorder may be checked every few hours, days or weeks to assess the further efficacy of the treatment. A decrease in extent or invasiveness of the cell proliferative disorder indicates that the treatment is efficacious. The method described may be used to screen or select patients that may benefit from treatment with an inhibitor of a cell proliferative disorder.

As used herein, "obtaining a biological sample from a subject," includes obtaining a sample for use in the methods described herein. A biological sample is described above.

Yet another aspect presents a method to identify a compound that modulates the phosphorylation of FAK, or specific domains thereof. The method may include obtaining the crystal structure of FAK, or specific domains thereof (optionally apo form or complexed) or obtaining the information relating to the crystal structure of a FAK, or specific domains thereof (optionally apo form or complexed), in the presence and/or absence of the test compound. Compounds may then be computer modeled into or on the FAK, or specific domains thereof binding site of the crystal structure to predict stabilization of the interaction between the FAK, or specific domains thereof and the test compound. Once potential modulating compounds are identified, the compounds may be screened using in vitro, in vivo, or cellular assays, such as the ones identified herein and competition assays known in the art. Compounds identified in this manner are useful as therapeutic agents.

In another aspect, a compound of the invention is packaged in a therapeutically effective amount with a pharmaceutically acceptable carrier or diluent. The composition may be formulated for treating a subject suffering from or susceptible to a cell proliferative disorder, and packaged with instructions to treat a subject suffering from or susceptible to a cell proliferative disorder.

In another aspect, the invention provides methods for inhibiting cell proliferation. In one embodiment, a method of inhibiting cell proliferation (or a cell proliferative disorder) according to the invention includes contacting cells with a compound capable of modulating FAK, FAK binding partner, or specific domains thereof. In either embodiment, the contacting may be in vitro, e.g., by addition of the compound to a fluid surrounding the cells, for example, to the growth media in which the cells are living or existing. The contacting may also be by directly contacting the compound to the cells. Alternately, the contacting may be in vivo, e.g., by passage of the compound through a subject; for example, after administration, depending on the route of administration, the compound may travel through the digestive tract or the blood stream or may be applied or administered directly to cells in need of treatment.

In another aspect, methods of inhibiting a cell proliferative disorder in a subject include administering an effective amount of a compound of the invention (i.e., a compound described herein) to the subject. The administration may be by any route of administering known in the pharmaceutical arts. The subject may have a cell proliferative disorder, may be at risk of developing a cell proliferative disorder, or may need prophylactic treatment prior to anticipated or unanticipated exposure to a conditions capable of increasing susceptibility to a cell proliferative disorder, e.g., exposure to carcinogens or to ionizing radiation.

In one aspect, a method of monitoring the progress of a subject being treated with a compound herein includes determining the pre-treatment status (e.g., size, growth rate, or invasiveness of a tumor) of the cell proliferative disorder, administering a therapeutically effective amount of a compound herein to the subject, and determining the status (e.g., size, growth rate, or invasiveness of a tumor) of the cell proliferative disorder after an initial period of treatment with the compound, wherein the modulation of the status indicates efficacy of the treatment.

The subject may be at risk of a cell proliferative disorder, may be exhibiting symptoms of a cell proliferative disorder, may be susceptible to a cell proliferative disorder and/or may have been diagnosed with a cell proliferative disorder.

If the modulation of the status indicates that the subject may have a favorable clinical response to the treatment, the subject may be treated with the compound. For example, the subject can be administered therapeutically effective dose or doses of the compound.

In another aspect, methods for evaluating a test compound comprise contacting FAK, or specific domains thereof with a test compound (complex), and evaluating the binding interaction following contact, wherein a change in the stability of the complex relative to a reference value is an indication that the test compound modulates the stability of the complex.

The FAK, or specific domains thereof complex may be modeled in silico, or may be a complex within a cell, isolated from a cell, recombinantly expressed, purified or isolated from a cell or recombinant expression system or partially purified or isolated from a cell or recombinant expression system.

Kits of the invention include kits for treating a cell proliferative disorder in a subject. The kit may include a compound of the invention, for example, a compound described herein, pharmaceutically acceptable esters, salts, and prodrugs thereof, and instructions for use. The instructions for use may include information on dosage, method of delivery, storage of the kit, etc. The kits may also include, reagents, for example, test compounds, buffers, media (e.g., cell growth media), cells, etc. Test compounds may include known compounds or newly discovered compounds, for example, combinatorial libraries of compounds. One or more of the kit of the invention may be packaged together, for example, a kit for assessing the efficacy of an treatment for a cell proliferative disorder may be packaged with a kit for monitoring the progress of a subject being treated for a cell proliferative disorder according to the invention.

The present methods can be performed on cells in culture, e.g. in vitro or ex vivo, or on cells present in an animal subject, e.g., in vivo. Compounds of the inventions can be initially tested in vitro using primary cultures of proliferating cells, e.g., transformed cells, tumor cell lines, and the like.

The present method can be performed on cells in culture, e.g. in vitro or ex vivo, or on cells present in an animal subject, e.g., in vivo. Compound of the invention can be initially tested in vitro using cells from the respiratory tract from embryonic rodent pups (See e.g. U.S. Pat. No. 5,179,109—fetal rat tissue culture), or other mammalian (See e.g. U.S. Pat. No. 5,089,517—fetal mouse tissue culture) or non-mammalian animal models.

Alternatively, the effects of compound of the invention can be characterized in vivo using animals models.

4. Pharmaceutical Compositions

The invention also provides a pharmaceutical composition, comprising an effective amount of a compound described herein and a pharmaceutically acceptable carrier. In a further embodiment, the effective amount is effective to treat a cell proliferative disorder, as described previously.

In an embodiment, the compound of the invention is administered to the subject using a pharmaceutically-acceptable formulation; e.g., a pharmaceutically-acceptable formulation that provides sustained delivery of the compound of the invention to a subject for at least 12 hours, 24 hours, 36 hours, 48 hours, one week, two weeks, three weeks, or four weeks after the pharmaceutically-acceptable formulation is administered to the subject.

In certain embodiments, these pharmaceutical compositions are suitable for topical or oral administration to a subject. In other embodiments, as described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes; (2) parenteral administration, for example, by subcutaneous, intramuscular or intravenous injection as, for example, a sterile solution or suspension; (3) topical application, for example, as a cream, ointment or spray applied to the skin; (4) intravaginally or intrarectally, for example, as a pessary, cream or foam; or (5) aerosol, for example, as an aqueous aerosol, liposomal preparation or solid particles containing the compound.

The phrase "pharmaceutically acceptable" refers to those compound of the inventions of the present invention, compositions containing such compounds, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" includes pharmaceutically-acceptable material, composition or vehicle, such as a liquid or solid filler, diluent, excipient, solvent or encapsulating material, involved in carrying or transporting the subject chemical from one organ, or portion of the body, to another organ, or portion of the body. Each carrier is "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Compositions containing a compound of the invention(s) include those suitable for oral, nasal, topical (including buccal and sublingual), rectal, vaginal, aerosol and/or parenteral administration. The compositions may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, more preferably from about 10 percent to about 30 percent.

Methods of preparing these compositions include the step of bringing into association a compound of the invention(s) with the carrier and, optionally, one or more accessory ingredients. In general, the formulations are prepared by uniformly and intimately bringing into association a compound of the invention with liquid carriers, or finely divided solid carriers, or both, and then, if necessary, shaping the product.

Compositions of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the invention(s) as an active ingredient. A compound may also be administered as a bolus, electuary or paste.

In solid dosage forms of the invention for oral administration (capsules, tablets, pills, dragees, powders, granules and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered active ingredient moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compound of the invention(s) include pharmaceutically-acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

In addition to inert diluents, the oral compositions can include adjuvants such as wetting agents, emulsifying and suspending agents, sweetening, flavoring, coloring, perfuming and preservative agents.

Suspensions, in addition to the active compound of the invention(s) may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Pharmaceutical compositions of the invention for rectal or vaginal administration may be presented as a suppository, which may be prepared by mixing one or more compound of the invention(s) with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active agent.

Compositions of the present invention which are suitable for vaginal administration also include pessaries, tampons, creams, gels, pastes, foams or spray formulations containing such carriers as are known in the art to be appropriate.

Dosage forms for the topical or transdermal administration of a compound of the invention(s) include powders, sprays, ointments, pastes, creams, lotions, gels, solutions, patches and inhalants. The active compound of the invention(s) may be mixed under sterile conditions with a pharmaceutically-acceptable carrier, and with any preservatives, buffers, or propellants which may be required.

The ointments, pastes, creams and gels may contain, in addition to compound of the invention(s) of the present invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of the invention(s), excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

The compound of the invention(s) can be alternatively administered by aerosol. This is accomplished by preparing an aqueous aerosol, liposomal preparation or solid particles containing the compound. A nonaqueous (e.g., fluorocarbon propellant) suspension could be used. Sonic nebulizers are preferred because they minimize exposing the agent to shear, which can result in degradation of the compound.

Ordinarily, an aqueous aerosol is made by formulating an aqueous solution or suspension of the agent together with conventional pharmaceutically-acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Transdermal patches have the added advantage of providing controlled delivery of a compound of the invention(s) to the body. Such dosage forms can be made by dissolving or dispersing the agent in the proper medium. Absorption enhancers can also be used to increase the flux of the active ingredient across the skin. The rate of such flux can be controlled by either providing a rate controlling membrane or dispersing the active ingredient in a polymer matrix or gel.

Ophthalmic formulations, eye ointments, powders, solutions and the like, are also contemplated as being within the scope of the invention.

Pharmaceutical compositions of the invention suitable for parenteral administration comprise one or more compound of the invention(s) in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers, which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of compound of the invention(s) in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compound of the invention(s) are administered as pharmaceuticals, to humans and animals, they can be given per se or as a pharmaceutical composition containing, for example, 0.1 to 99.5% (more preferably, 0.5 to 90%) of active ingredient in combination with a pharmaceutically-acceptable carrier.

Regardless of the route of administration selected, the compound of the invention(s), which may be used in a suitable hydrated form, and/or the pharmaceutical compositions of the present invention, are formulated into pharmaceutically-acceptable dosage forms by conventional methods known to those of skill in the art.

Actual dosage levels and time course of administration of the active ingredients in the pharmaceutical compositions of the invention may be varied so as to obtain an amount of the active ingredient which is effective to achieve the desired therapeutic response for a particular patient, composition, and mode of administration, without being toxic to the patient. An exemplary dose range is from 0.1 to 10 mg per day.

A preferred dose of the compound of the invention for the present invention is the maximum that a patient can tolerate and not develop serious side effects. Preferably, the compound of the invention of the present invention is administered at a concentration of about 0.001 mg to about 100 mg per kilogram of body weight, about 0.001-about 10 mg/kg or about 0.001 mg-about 100 mg/kg of body weight. Ranges intermediate to the above-recited values are also intended to be part of the invention.

6. Screening Methods and Systems

In another aspect, the invention provides a machine readable storage medium which comprises the structural coordinates of either one or both of the binding pockets identified herein, or similarly shaped, homologous binding pockets. Such storage medium encoded with these data are capable of displaying a three-dimensional graphical representation of a molecule or molecular complex which comprises such binding pockets on a computer screen or similar viewing device.

The invention also provides methods for designing, evaluating and identifying compounds which bind to the aforementioned binding pockets. Thus, the computer produces a three-dimensional graphical structure of a molecule or a molecular complex which comprises a binding pocket.

In another embodiment, the invention provides a computer for producing a three-dimensional representation of a molecule or molecular complex defined by structure coordinates of FAK, or domains thereof, or a three-dimensional representation of a homologue of said molecule or molecular complex, wherein said homologue comprises a binding pocket that has a root mean square deviation from the backbone atoms of said amino acids of not more than 2.0 (more preferably not more than 1.5) angstroms In exemplary embodiments, the computer or computer system can include components which are conventional in the art, e.g., as disclosed in U.S. Pat. No. 5,978,740 and/or U.S. Pat. No. 6,183,121 (incorporated herein by reference). For example, a computer system can includes a computer comprising a central processing unit ("CPU"), a working memory (which may be, e.g., RAM (random-access memory) or "core" memory), a mass storage memory (such as one or more disk drives or CD-ROM drives), one or more cathode-ray tube (CRT) or liquid crystal display (LCD) display terminals, one or more keyboards, one or more input lines, and one or more output lines, all of which are interconnected by a conventional system bus.

Machine-readable data of this invention may be inputted to the computer via the use of a modem or modems connected by a data line. Alternatively or additionally, the input hardware may include CD-ROM drives, disk drives or flash memory. In conjunction with a display terminal, a keyboard may also be used as an input device.

Output hardware coupled to the computer by output lines may similarly be implemented by conventional devices. By way of example, output hardware may include a CRT or LCD display terminal for displaying a graphical representation of a binding pocket of this invention using a program such as QUANTA or PYMOL. Output hardware might also include a printer, or a disk drive to store system output for later use.

In operation, the CPU coordinates the use of the various input and output devices, coordinates data accesses from the mass storage and accesses to and from working memory, and determines the sequence of data processing steps. A number of programs may be used to process the machine-readable data of this invention, including commercially-available software.

A magnetic storage medium for storing machine-readable data according to the invention can be conventional. A magnetic data storage medium can be encoded with a machine-readable data that can be carried out by a system such as the computer system described above. The medium can be a conventional floppy diskette or hard disk, having a suitable substrate which may be conventional, and a suitable coating, which may also be conventional, on one or both sides, containing magnetic domains whose polarity or orientation can be altered magnetically. The medium may also have an opening (not shown) for receiving the spindle of a disk drive or other data storage device.

The magnetic domains of the medium are polarized or oriented so as to encode in manner which may be conventional, machine readable data such as that described herein, for execution by a system such as the computer system described herein.

An optically-readable data storage medium also can be encoded with machine-readable data, or a set of instructions, which can be carried out by a computer system. The medium can be a conventional compact disk read only memory (CD-ROM) or a rewritable medium such as a magneto-optical disk which is optically readable and magneto-optically writable.

In the case of CD-ROM, as is well known, a disk coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, a data-recording coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Structure data, when used in conjunction with a computer programmed with software to translate those coordinates into the 3-dimensional structure of a molecule or molecular complex comprising a binding pocket may be used for a variety of purposes, such as drug discovery.

For example, the structure encoded by the data may be computationally evaluated for its ability to associate with chemical entities. Chemical entities that associate with a binding pocket of a FAK, or specific domains thereof, and are potential drug candidates. Alternatively, the structure encoded by the data may be displayed in a graphical three-dimensional representation on a computer screen. This allows visual inspection of the structure, as well as visual inspection of the structure's association with chemical entities.

Thus, according to another embodiment, the invention relates to a method for evaluating the potential of a chemical entity to associate with a) a molecule or molecular complex comprising a binding pocket of FAK, or specific domains thereof, or b) a homologue of said molecule or molecular complex, wherein said homologue comprises a binding pocket that has a root mean square deviation from the backbone atoms of said amino acids of not more than 2.0 (more preferably 1.5) angstroms.

This method comprises the steps of:

i) employing computational means to perform a fitting operation between the chemical entity and a binding pocket of the molecule or molecular complex; and ii) analyzing the results of the fitting operation to quantify the association between the chemical entity and the binding pocket. The term "chemical entity", as used herein, refers to chemical compounds, complexes of at least two chemical compounds, and fragments of such compounds or complexes.

The design of compounds that bind to or inhibit FAK, or specific domains thereof binding pockets according to this invention generally involves consideration of several factors. First, the entity must be capable of physically and structurally associating with parts or all of the FAK, or specific domains thereof—related binding pockets. Non-covalent molecular interactions important in this association include hydrogen bonding, van der Waals interactions, hydrophobic interactions and electrostatic interactions. Second, the entity must be able to assume a conformation that allows it to associate with the FAK, or specific domains thereof—related binding pocket(s) directly. Although certain portions of the entity will not directly participate in these associations, those portions of the entity may still influence the overall conformation of the molecule. This, in turn, may have a significant impact on potency. Such conformational requirements include the overall three-dimensional structure and orientation of the chemical entity in relation to all or a portion of the binding pocket, or the spacing between functional groups of an entity comprising several chemical entities that directly interact with the binding pocket or homologues thereof.

The potential inhibitory or binding effect of a chemical entity on a FAK, or specific domains thereof—related binding pocket may be analyzed prior to its actual synthesis and testing by the use of computer modeling techniques. If the theoretical structure of the given entity suggests insufficient interaction and association between it and the target binding pocket, testing of the entity is obviated. However, if computer modeling indicates a strong interaction, the molecule may then be synthesized and tested for its ability to bind to a binding pocket. This may be achieved, e.g., by testing the ability of the molecule to inhibit FAK, or specific domains thereof activity, e.g., using assays described herein or known in the art. In this manner, synthesis of inoperative compounds may be avoided.

A potential inhibitor of a FAK, or specific domains thereof—related binding pocket may be computationally evaluated by means of a series of steps in which chemical entities or fragments are screened and selected for their ability to associate with the FAK, or specific domains thereof—related binding pockets.

One skilled in the art may use one of several methods to screen chemical entities or fragments for their ability to associate with a FAK, or specific domains thereof—related binding pocket. This process may begin by visual inspection of, for example, a FAK, or specific domains thereof—related binding pocket on the computer screen based on the FAK, or specific domains thereof structure coordinates described herein, or other coordinates which define a similar shape generated from the machine-readable storage medium. Selected fragments or chemical entities may then be positioned in a variety of orientations, or docked, within that binding pocket as defined supra. Docking may be accomplished using software such as Quanta and DOCK, followed by energy minimization and molecular dynamics with standard molecular mechanics force fields, such as CHARMM and AMBER.

Specialized computer programs (e.g., as known in the art and/or commercially available and/or as described herein) may also assist in the process of selecting fragments or chemical entities.

Once suitable chemical entities or fragments have been selected, they can be assembled into a single compound or complex. Assembly may be preceded by visual inspection of the relationship of the fragments to each other on the three-dimensional image displayed on a computer screen in relation to the structure coordinates of the target binding pocket.

Instead of proceeding to build an inhibitor of a binding pocket in a step-wise fashion one fragment or chemical entity at a time as described above, inhibitory or other binding compounds may be designed as a whole or "de novo" using either an empty binding site or optionally including some portion(s) of a known inhibitor(s). There are many de novo ligand design methods known in the art, some of which are commercially available (e.g., LeapFrog, available from Tripos Associates, St. Louis, Mo.).

Other molecular modeling techniques may also be employed in accordance with this invention [see, e.g., N. C. Cohen et al., "Molecular Modeling Software and Methods for Medicinal Chemistry, J. Med. Chem., 33, pp. 883-894 (1990); see also, M. A. Navia and M. A. Murcko, "The Use of Structural Information in Drug Design", Current Opinions in Structural Biology, 2, pp. 202-210 (1992); L. M. Balbes et al., "A Perspective of Modern Methods in Computer-Aided Drug Design", in Reviews in Computational Chemistry, Vol. 5, K. B. Lipkowitz and D. B. Boyd, Eds., VCH, New York, pp. 337-380 (1994); see also, W. C. Guida, "Software For Structure-Based Drug Design", Curr. Opin. Struct. Biology, 4, pp. 777-781 (1994)].

Once a compound has been designed or selected, the efficiency with which that entity may bind to a binding pocket may be tested and optimized by computational evaluation.

Specific computer software is available in the art to evaluate compound deformation energy and electrostatic interactions. Examples of programs designed for such uses include: AMBER; QUANTA/CHARMM (Accelrys, Inc., Madison, Wis.) and the like. These programs may be implemented, for instance, using a commercially-available graphics workstation. Other hardware systems and software packages will be known to those skilled in the art.

Another technique involves the in silico screening of virtual libraries of compounds, e.g., as described herein. Many thousands of compounds can be rapidly screened and the best virtual compounds can be selected for further screening (e.g., by synthesis and in vitro testing). Small molecule databases can be screened for chemical entities or compounds that can bind, in whole or in part, to a FAK, or specific domains thereof binding pocket. In this screening, the quality of fit of such entities to the binding site may be judged either by shape complementarity or by estimated interaction energy.

EXAMPLES

The invention is further illustrated by the following examples which are intended to illustrate but not limit the scope of the invention.

Materials

Cell lines and culture—BT474 breast carcinoma cells were maintained in RPMI1640 medium supplemented with 10% fetal bovine serum (FBS), 5 µg/ml insulin, and 1 µg/ml penicillin/streptomycin. The MCF-7 cell line was obtained from ATCC and maintained according to the manufacturer's protocol. Colon cancer cell lines, HT-29, were maintained in McCoy's 5A plus 10% FBS medium. MCF10A cells and other cancer cell lines were maintained according to ATCC protocol. Panc-1 and Miapaca-2 carcinoma cells, normal human fibroblasts and benign human breast epithelial cells were obtained from ATCC and maintained in RPMI1640 medium supplemented with 10% fetal bovine serum (FBS), 5 µg/ml insulin, and 1 µg/ml penicillin/streptomycin.

Small-Molecule Inhibitor Compounds—Thirty-six compounds that were detected by the DOCK program to best fit into the Y397 site of FAK were ordered from the National Cancer Institute, Developmental Therapeutics Program (NCI/DTP) free of charge. Each compound was solubilized in water or DMSO at concentration of 25 mM and stored at −20 C and −80 C. The Y15 compound was ordered from Sigma for biochemical analyses in vitro and injection into mice for in-vivo studies. Y15 was solubilized in water at concentration of 25 mM and stored at −20° C. and −80° C.

FAK inhibitors—FAK kinase inhibitor, NVP-TAE226 (called as TAE226) was obtained from Novartis Inc. (15). TAE226 was dissolved at DMSO at 25 mM. The structure and the therapeutic effect of compound are described in (15,16, 18). The TAE-226 inhibitor used as a control of FAK inhibition in the experiments. The TAE-226 inhibitor was used as a control for FAK inhibition in the in vitro experiments.

Antibodies—Monoclonal anti-FAK (4.47) antibody to N-terminal FAK and monoclonal anti-paxillin antibody were obtained from Upstate Biotechnology, Inc. Polyclonal anti-phospho-Tyr397-FAK and anti-phospho Tyr-418-Src antibodies were from Biosource Inc. Monoclonal anti-caspase-3 antibodies were ordered from Transduction Labs. Monoclonal anti-α-tubulin and β-actin antibodies were obtained from Sigma. Polyclonal anti c-Src antibody was from Santa Cruz Inc. and used for Western blotting. Monoclonal anti-Src antibody (clone 327) was used from Oncogene Research Products Inc. Monoclonal and ERK antibodies were obtained from Millipore (Lake Placid, N.Y.). Antibodies to caspase-3 and Ki67 were obtained from DAKO (Carpinteria, Calif.) and Cell Signaling (Danvers, Mass.), respectively.

Example 1

Structure-Based Molecular Docking of Potential FAK Small-Molecule Inhibitors The crystal structure of FAK, N-terminal FERM domain (20) was used for docking of FAK inhibitors. We used a structure-based approach combining molecular docking with functional testing. 20,000 small-molecule compounds with drug-like characteristics (following the Lipinski rules) were docked into the N-terminal domain of FAK domain of the human FAK crystal structure in 100 different orientations using DOCK5.1. Pyk2 and FAK share a similar structural organization with a tyrosine kinase domain flanked by non-catalytic domains at both the N and C termini. These two kinases are approximately 60% identical in the central catalytic domain and share approximately 40% identity in both the N- and C-terminal domains. Because of the high sequence homology and similar overall organization between Pyk2 and FAK, it is especially interesting to compare the interaction of Y15 with both of these molecules. Following Lipinski rules, Y15 was docked into the N-terminal domains of FAK and Pyk2 utilizing their humancrystal structures in 100 different orientations using DOCK5.1 program, as described previously. Docking calculations were performed on the University of Florida High Performance Computing supercomputing cluster using 16 processors (http://hpc.ufl.edu).

All docking calculations were performed with the University of California, San Francisco DOCK 5.1. program, using a clique-matching algorithm to orient Y15 to the Y397 site of FAK and amino terminus of Pyk2. The files for hydrogen atoms and partial charges were created using SYBDB program.

Example 2

Cell Viability Assay—The Cells were treated with peptides for 24 hours at different peptide concentrations. The 3-(4,5-dimethylthiazol-2-yl)-5-(3-carboxymethoxyphenyl)-2-(4-sulfophenyl)-2H-tetrazolium compound from Promega Viability kit (Madison, Ill.) was added, and the cells were incubated at 37° C. for 1-2 hours. The optical density on 96-plate was analyzed with a microplate reader at 490 nm to determine cell viability. In addition, cells were stained with trypan blue after 24 hours of treatment with Y15 and the percent of cells that stained positive were determined with a hemacytometer.

Cell adhesion assay—The poly-L-Lysine or Collagen (5 μg/ml) coated 96-well plates were blocked with the blocking buffer (medium with 0.5% BSA) for 1 hour at 37 C. The cells were pre-treated with drugs for 3 hours and plated for adhesion at $4 \times 10^5$ cells. Cells were incubated at 37 C for 1 hour, fixed in 3.7% formaldehyde, washed in 0.1% BSA in PBS and stained with crystal violet (5 mg/ml in 2% ethanol) for 10 minutes. Then 2% SDS was added to the dried plated and OD at 590 nm was measured for detecting cell adhesion.

Western Blotting—Cells or homogenized tumor samples were washed twice with cold 1×PBS and lysed on ice for 30 minutes in a buffer containing: 50 mM Tris-HCl (pH 7.5), 150 mM NaCl, 1% Triton-X, 0.5% NaDOC, 0.1% SDS, 5 mM EDTA, 50 mM NaF, 1 mM NaVO3, 10% glycerol and protease inhibitors: 10 μg/ml leupeptin, 10 μg/ml PMSF and 1 μg/ml aprotinin. The lysates were cleared by centrifugation at 10,000 rpm for 30 minutes at 4° C. Protein concentrations were determined using a Bio-Rad Kit. The boiled samples were loaded on Ready SDS-10% PAGE gels (Bio Rad, Inc) and used for Western blot analysis with the protein-specific antibody. Immunoblots were developed with chemiluminescence Renaissance reagent (NEN Life Science Products, Inc).

Immunoprecipitation. Immunoprecipitation was performed according to the standard protocol. In brief, the pre-cleared lysates with equal amount of protein were incubated with 1 μg of primary antibody and 30 μl A/G agarose beads overnight at 4° C. The precipitates were washed with lysis buffer three times and re-suspended in 2× Laemmli buffer. The boiled samples were used for Western blotting, as described above.

Detachment Assay—Cells were plated with and without inhibitors for 24 hours, and detached and attached cells were counted in a hemocytometer. We calculated the percent of detachment by dividing the number of detached cells by the total number of cells. The percent of detached cells was calculated in three independent experiments.

Apoptosis Assay. Detached cells were collected and fixed in 3.7% formaldehyde in 1×PBS solution for the apoptosis assay. Detection of apoptosis was done with Hoechst 33342 staining. The percent of apoptotic cells was calculated as a ratio of apoptotic detached cells divided by the total number of cells in three independent experiments in several fields with the fluorescent microscope. For each experiment 300 cells per treatment were counted.

In vitro Kinase Assay—10 μCi of $[\gamma-^{32}P]$-ATP in a kinase buffer (20 mM HEPES, pH 7.4, 5 mM $MgCl_2$, 5 mM $MnCl_2$, 0.1 mM $Na_3VO_4$ with 0.1 μg of purified FAK protein were incubated in a kinase buffer with 10 μCi of $[\gamma-^{32}P]$-ATP. The kinase reaction was performed for 5 minutes at room temperature and stopped by addition of 2× Laemmli buffer. Proteins were separated on a Ready SDS-10% PAGE gel, and the phosphorylated enolase was visualized by autoradiography.

KinaseProfiler screening—Kinase specificity screening was performed with KinaseProfiler™ Service (Millipore) available on http://www.millipore.com/drugdiscovery/dd3/KinaseProfiler. The screening was performed with 1 μM Y15, 10 μM ATP and kinase substrates on 9 recombinant kinases according to Millipore protocol.

Tumor Growth in Nude Mice—Female nude mice, 6 weeks old, were purchased from Harlan Laboratory. The mice were maintained in the animal facility and all experiments were performed in compliance with NIH animal-use guidelines and IACUC protocol approved by the UF Animal Care Committee. BT474 cells were injected, 2 millions cells/injection subcutaneously. The day after injection, the drug was introduced by IP injection at 30 mg/kg dose daily 5 days/week for 3 weeks. Panc-1 cells were injected, $2 \times 10^6$ cells/injection, subcutaneously. In preliminary experiment different doses of the compound were introduced into the mice, and 30 mg/kg was chosen as optimal, non-toxic dose. The ability of this dose to inhibit tumor growth was determined. The day after tumor inoculation, the compound was introduced by IP injection at 30 mg/kg dose daily 5 days/week for 3 weeks. Subsequently, the effect of this compound in the presence of gemcitabine chemotherapy was evaluated. Tumor diameters were measured with calipers and tumor volume in $mm^3$ was calculated using this formula=$(width)^2 \times Length/2$. At the end of experiment, tumor weight and volume was determined.

Immunohistochemistry Staining—FAK staining was performed with Y397-antibody on slides with paraffin-embedded tumor samples, as described previously (21). Immunohistochemistry staining for caspase-3 (1:400 dilution) and Ki67 (1:500 dilution) was performed on slides with paraffin-embedded tumor samples (see, Golubovskaya V M, Finch R, Kweh F, Massoll N A, Campbell-Thompson M, Wallace M R, Cance W G. p53 regulates FAK expression in human tumor cells. Mol Carcinog 2007; 47:373-82).

Statistical Analyses—Student's t test was performed, when appropriate, to determine significance. The difference between data with P<0.05 was considered significant.

Example 3

Targeting Y397 Site of FAK by Structure-Based Molecular Docking Approach and NCI Database Screening Reveals Y397 Drugs that Decrease Cell Viability The crystal structure of the N-terminal (FERM) domain of FAK has been recently identified (20). Instead of high-throughput screening, we used a structure-based approach combining molecular docking and functional testing. More than 20,000 compounds with known three-dimensional structure were docked into the structural pocket of FAK containing Y397 site. This approach combined the NCI/DTP (atomic coordinates and small molecules) database with improved molecular docking and scoring algorithms of DOCK 5.1 program (19). Each of 20,000 small-molecule compounds was docked in 100 different orientations using DOCK 5.1.0. As an example, one of such docked compound in the Y397 site of FAK is shown on FIG. 1. The 36 compounds of >20,000 compounds that had the highest scores of interaction with Y397 FAK were ordered from NCI and tested for the effect on cancer cell viability by MTT assay.

Y15 was docked onto the amino terminus of Pyk2, which is a FAK homologue. Utilizing van del Waals charges and electrostatic forces, the highest scoring for Y15 docking onto Pyk2 was −14.2. Note the pocket that binds Y15 in FAK is absent on Pyk2. The score demonstrating the docking of Y15 onto FAK (−38.5) is much higher than for Pyk2.

We tested 6 different cancer cell lines: BT474, T47D, MCF-7 breast cancer cells lines, HT29 colon cancer, C8161 melanoma, and A549 lung cancer cell lines with the 36 compounds, targeting the Y397 site of FAK. One of these compounds, Y15 compound, maximally decreased cell viability in all cancer cell lines (FIG. 2 A, B). FIG. 2 shows decreased viability in T47D breast cancer (FIG. 2A) and C8161 melanoma cancer cells (FIG. 2B) and is compared with the known FAK catalytic inhibitor TAE226 (Novartis). Y15 effectively blocked cell viability in resistant breast cancer cells with overexpressed Src and activated FAK (not shown). The structure of Y15, docking to Y397 site, and the name of this compound is 1,2,4,5-benzenetetraamine tetrahydrochloride are shown on FIG. 3 (for simplicity in the text we will call this compound Y15).

Example 4

Figure 4A:
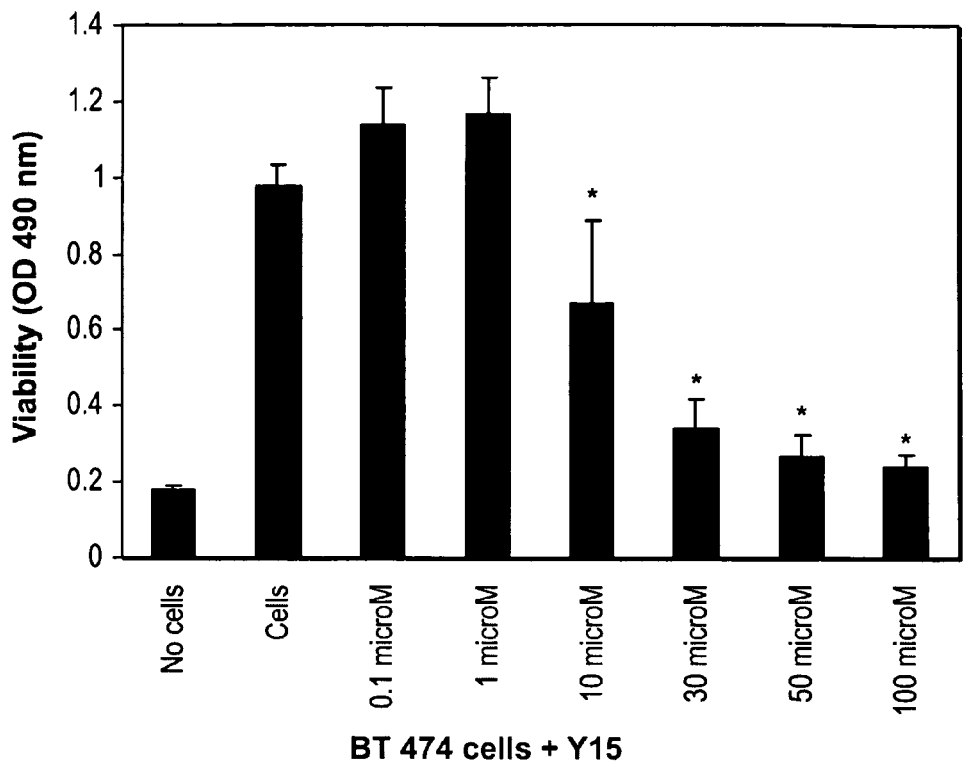
FIGS. 4A, B, C, D illustrate that Y15 inhibits cell viability and decreases Y397 FAK phosphorylation in a dose-dependent manner.

1,2,4,5-benzenetetraamine tetrahydrochloride (Y15) Inhibits Cell Viability in a Dose-Dependent Manner To determine whether 1,2,4,5-benzenetetraamine tetrahydrochloride (Y15) inhibits cell viability in a dose-dependent manner, we performed MTT assay with different doses 0, 0.1; 1; 10, 30; 50, and 100 μM of Y15 (FIG. 4A). The viability of BT474 cells started to decrease at 10 μM dose and was significantly blocked at 50-100 μM doses of Y15 drug. Thus, Y15 blocks cancer cell viability in a dose-dependent manner.

Using MTT, the effect of Y15 on pancreatic tumor cell viability at 72 hours was studied. Y15 inhibited pancreatic cancer cell viability starting at a dose of 1 μM and increased with higher doses. (FIGS. 8A, 8B) Thus, Y15 inhibits viability of pancreatic cells in a dose-dependent manner. The effects of Y15 were compared in FAK null and wildtype fibroblasts. Starting at a dose of 0.1 μM, Y15 decreased viability of FAK wildtype fibroblasts as compared to FAK null fibroblasts (p<0.05, FIG. 8C). This demonstrates the importance of the presence of FAK for Y15 to have its effects.

Example 5

Figures 4B, 4C:
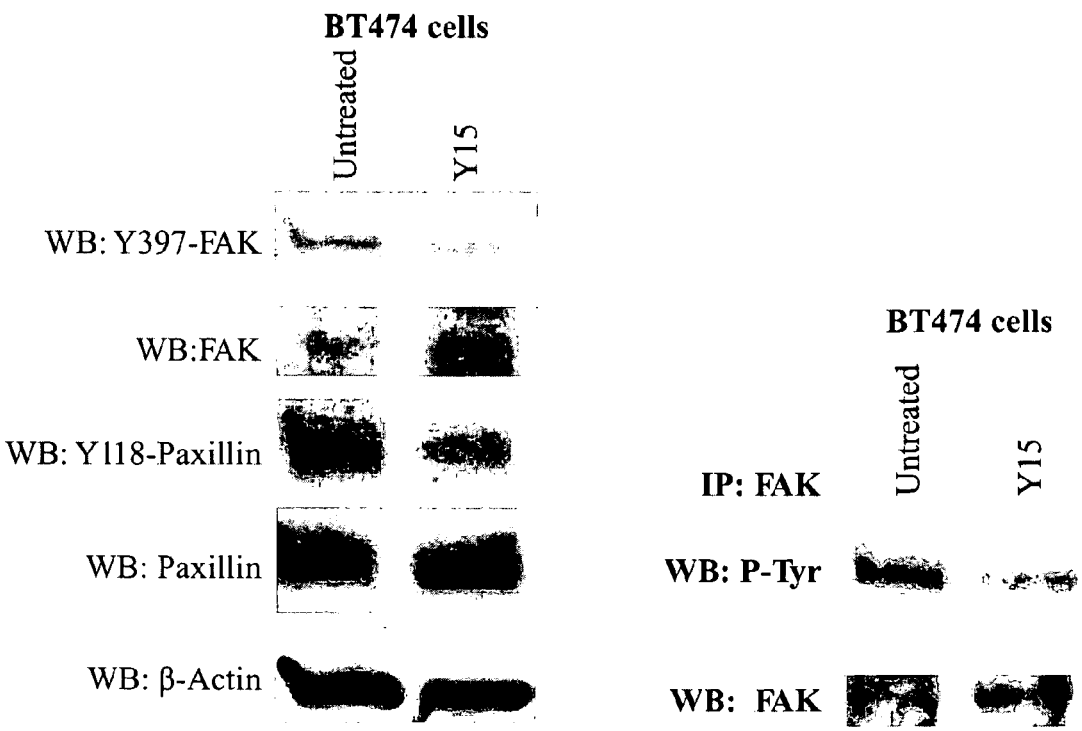
FIG. 4.
FIG. 4E illustrates that Y15 inhibits FAK autophosphorylation in a time-dependent manner.

1,2,4,5-benzenetetraamine tetrahydrochloride (Y15) Specifically Blocks Y397-FAK Phosphorylation To test the effect of Y15 on Y397 phosphorylation, we treated BT474 breast cancer cells with Y15 at 100 μM dose and performed Western blotting with Y397 FAK antibody (FIG. 4B). Y15 specifically inhibited Y397 phosphorylation of FAK and also phosphorylation of FAK down-stream substrate paxillin, Y118-paxillin (FIG. 4B). Y15 did not inhibit phosphorylation of other proteins, such as VEGFR-3 and c-Src (not shown). Thus, the effect of Y15 was specific to FAK. To test the effect of Y15 on total FAK autophosphorylation activity, we immunoprecipitated FAK and performed Western blotting with P-tyrosine antibody (FIG. 4C). Thus, Y15 that targets Y397 of FAK and decreases cell viability specifically inhibits Y397 and total FAK phosphorylation.

Example 6

Figure 4D:
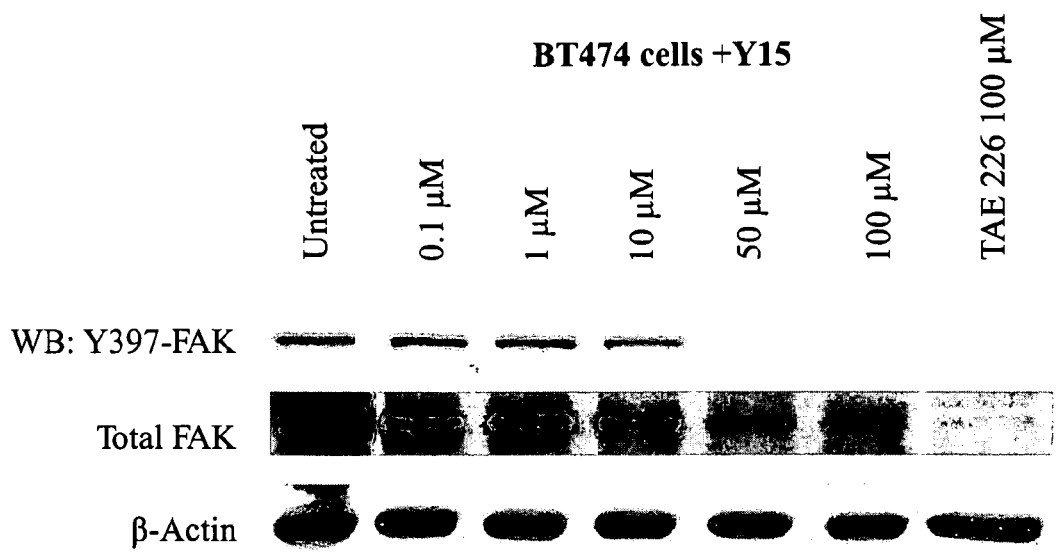

1,2,4,5-benzenetetraamine tetrahydrochloride (Y15) Blocks FAK Autophosphorylation in a Dose-Dependent Manner Next we analyzed the effect of Y15 on inhibiting FAK Y397 phosphorylation in a dose-dependent manner. We treated BT474 breast cancer cells with 0, 0.1, 1, 10, 50 and 100 μM of Y15 drug for 24 hours and performed Western blotting with Y397 antibody (FIG. 4D). Y15 decreased Y397 phosphorylation in a dose-dependent manner with high and maximal inhibition detected at 50 μM and 100 μM doses respectively that is consistent with the effect on cell viability. At 100 μM dose Y15 had the same inhibition as TAE226 inhibitor (Novartis) (FIG. 4D). Thus, Y15 drug, 1,2,4,5-benzenetetraamine tetrahydrochloride, inhibits FAK in a dose-dependent manner.

Figure 9A:
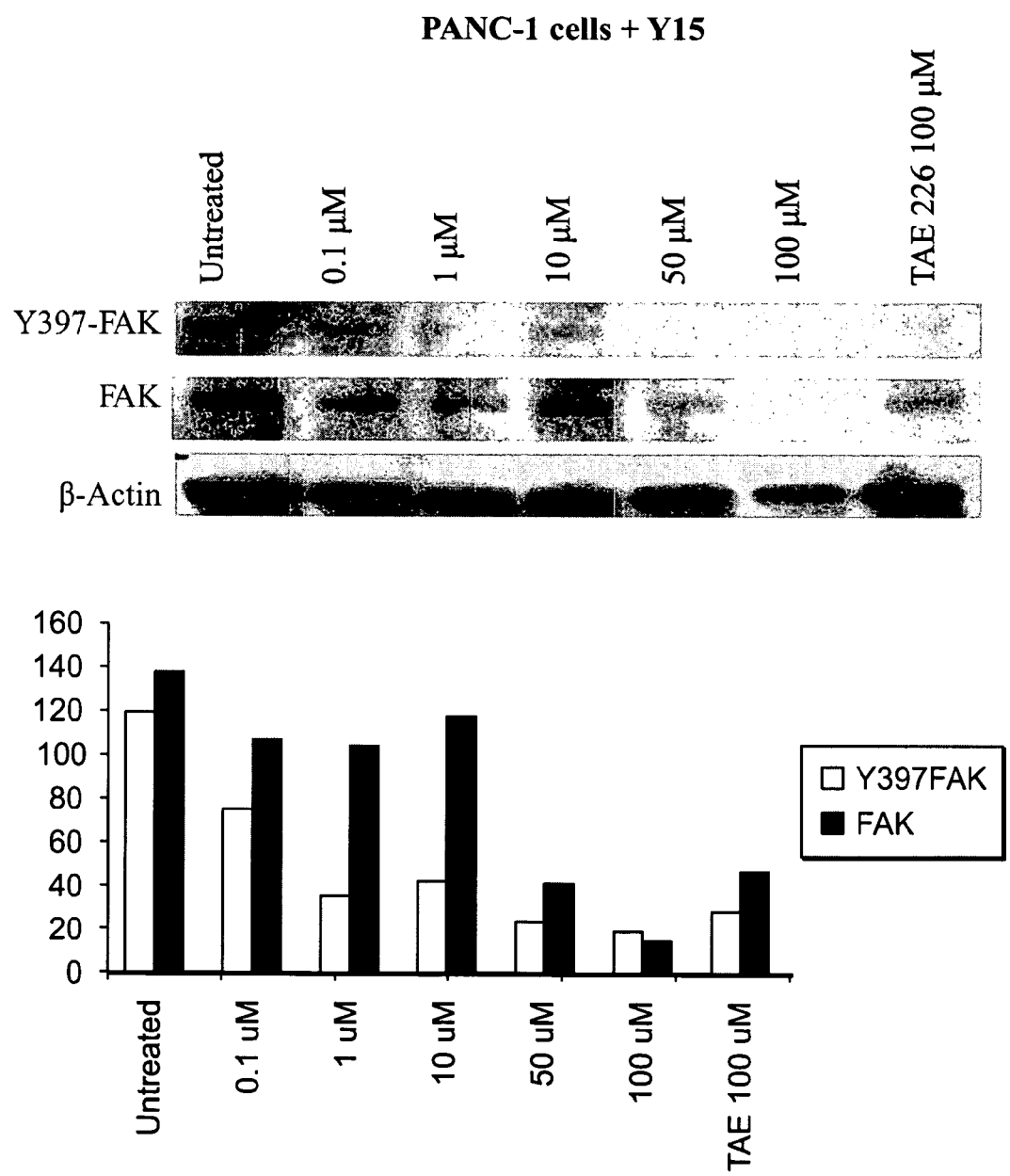
FIGS. 9A, B illustrate the effect of Y15 on FAK and ERK phosphorylation.
Figure 9B:
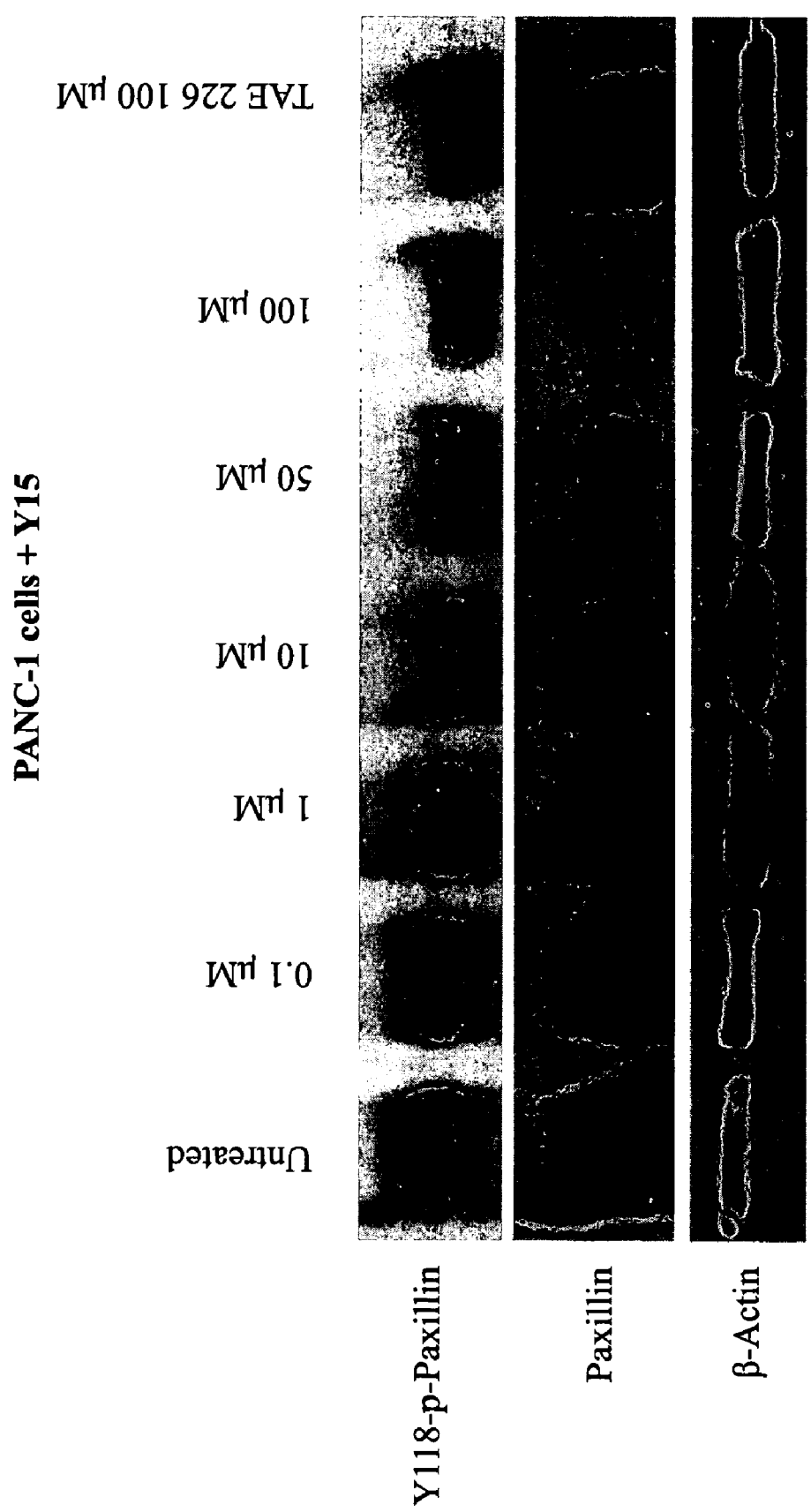
FIG. 9.

To test the effect of Y15 on Y397 phosphorylation, we treated Panc-1 pancreatic cancer cells with Y15 at increasing doses or TAE226 for 24 hours and performed Western blotting with Y397 FAK antibody (FIG. 9A). Y15 inhibited Y397 phosphorylation of FAK starting at 0.1 μM in Panc-1 cells. At a dose of 100 μM, Y15 had the same or better inhibition as TAE226. Of note, total FAK is down regulated at higher doses of Y15. Y15 also blocked phosphorylation of the FAK downstream substrate, paxillin (FIG. 9B). Total paxillin was decreased at higher doses similar to FAK. Thus, Y15, 1,2,4, 5-Benzenetetraamine tetrahydrochloride, inhibits FAK phosphorylation in a dose-dependent manner. Similar results were seen for Miapaca-2 cells.

Example 7

Figure 4E:
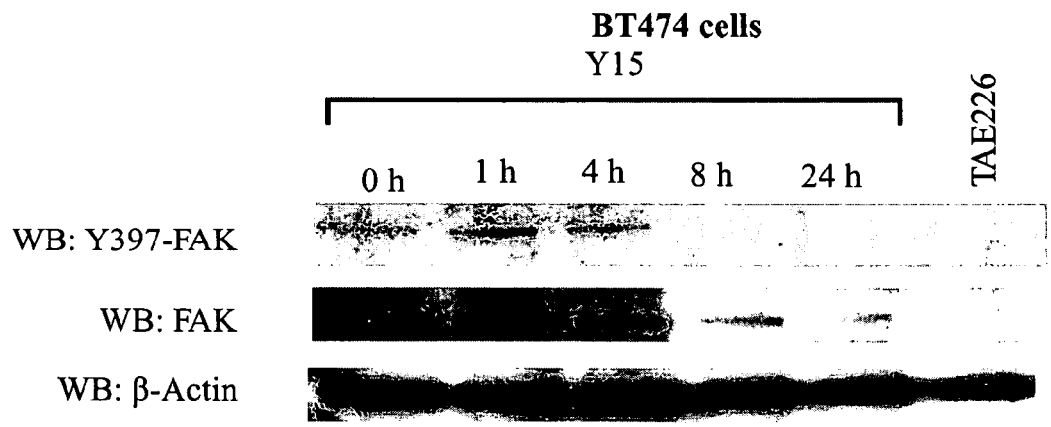

1,2,4,5-benzenetetraamine tetrahydrochloride (Y15) Blocks FAK Autophosphorylation in a Time-Dependent Manner Next we analyzed whether Y15 inhibits FAK Y397 phosphorylation in time-dependent manner. We treated BT474 cells with 100 μM of Y15 for 0, 1, 4, 8 and 24 hours, then Western blotting was performed with Y397 antibody (FIG. 4E). The result shows that treatment of Y15 at 4 hours did not significantly decreased Y397 phosphorylation, but 8 hours was enough to completely block Y397-phosphorylation and to down-regulate FAK. The control inhibitors TAE226 (Novartis) at 100 μM also completely blocked Y397 phosphorylation. Similarly to Y15 drug, TAE226 also down-regulated total FAK (FIG. 4E). Thus, the data demonstrate that Y15 inhibits FAK Y397 phosphorylation and down-regulates FAK in a time-dependent manner.

Example 8

Figure 5:
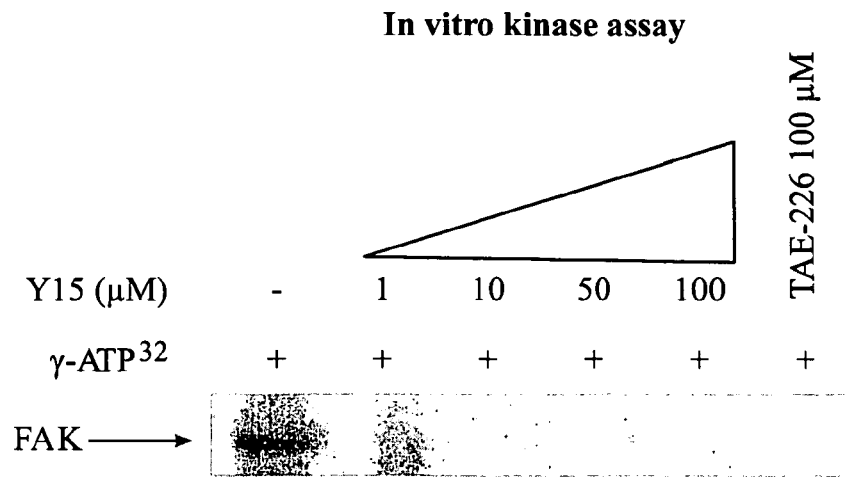
FIG. 5.

1,2,4,5-benzenetetraamine tetrahydrochloride (Y15) is a Direct FAK Autophosphorylation Inhibitor To test, whether Y15 is a direct inhibitor of FAK, we performed in vitro kinase assay with recombinant isolated with Baculovirus system purified FAK protein, described in (22). We performed in vitro kinase assay with 1-100 μM doses. We used TAE226 (Novartis) inhibitor as a positive control. Y15 directly blocked autophosphorylation activity of FAK starting from 1 dose, as well as control TAE226 (FIG. 5). In addition, Y15 was screened by in vitro kinase assay with 9 other recombinant commercially available kinases (c-RAF, c-Src, EGFR, VEGFR-3, IGF-1, Met, PDGFR-α, Pyk2, PI3K (p110δ/p85α) (Upstate Biotechnology, Inc), as described in Materials and Methods. Y15 did not significantly decrease kinase activity with the other kinases at 1 μM dose, as with FAK (FIG. 5). Thus, Y15 is a direct and specific inhibitor of FAK autophosphorylation.

Example 9

Figure 6A:
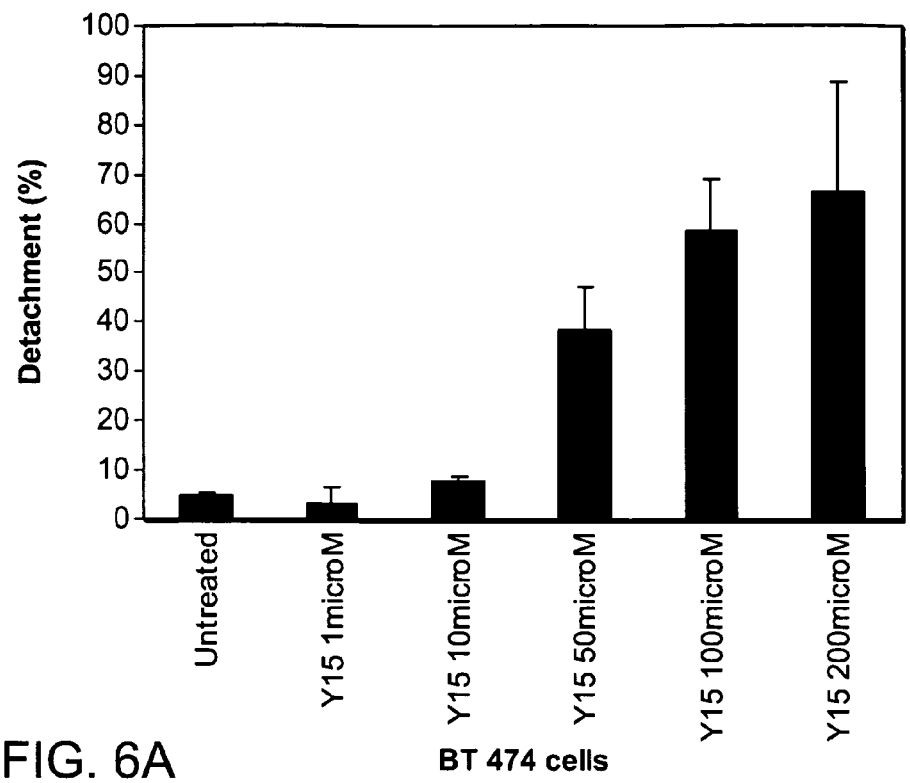
FIG. 6A illustrates that Y15 causes dose-dependent cell detachment in BT474 cells.

1,2,4,5-benzenetetraamine tetrahydrochloride (Y15) Causes Dose-Dependent Cell Detachment but is Non-Cytotoxic to Cells at High Concentrations that Inhibit FAK Autophosphorylation To test the cytotoxic effect of Y15 drug on breast cancer cells, we treated BT474 cells with Y15 drug at 1 and 100 μM for 24 hours. We performed analysis of detachment and apoptosis in Y15-treated BT474 cells (FIG. 6A). Y15 caused dose-dependent detachment in BT474 cells (FIG. 6A). At 10 μM dose, Y15 caused only 8% detachment in BT474 cells, while at 50 μM dose, detachment was equal to 38%. At 100-200 μM dose, detachment reached 58%-66% respectively. Y15 caused less detachment than TAE226 (Novartis) inhibitor, which induced 30% detachment at 10 μM and >80% detachment at 50 μM dose. Thus, Y15 effectively caused dose-dependent cellular detachment.

Figure 6B:
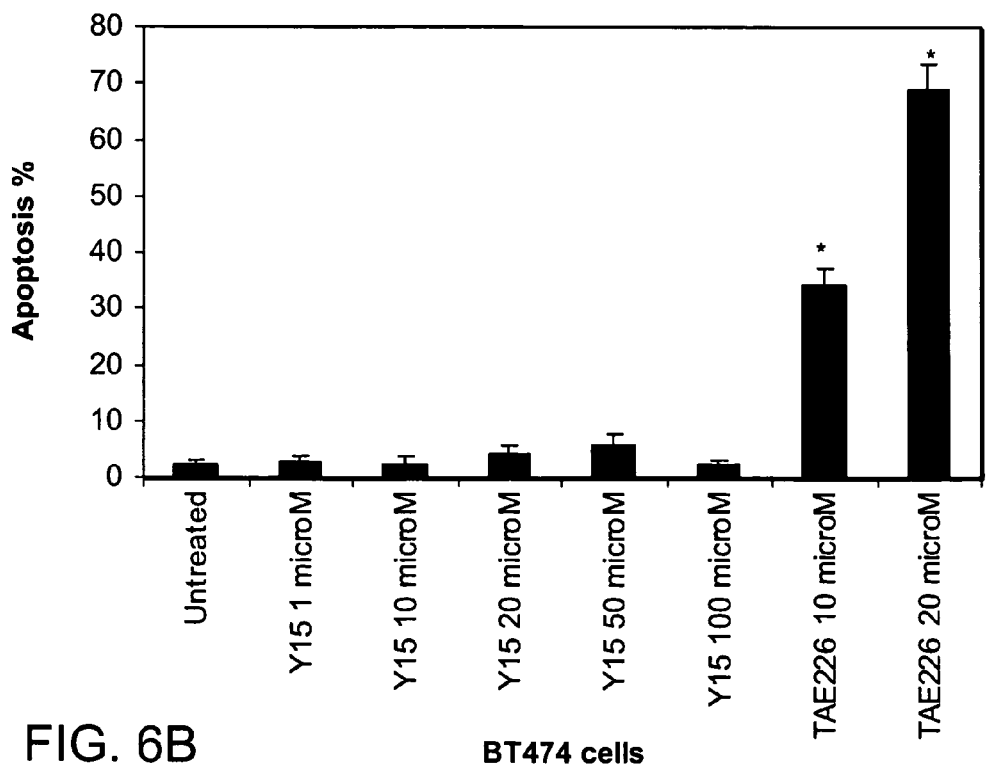
FIG. 6B illustrates that Y15 doesn't cause significant apoptosis in BT474 cells.

To test the effect of Y15 on apoptosis, we performed Hoechst staining on untreated and treated with Y15 cells. At high 50-100 μM dose, Y15 did not cause significant apoptosis in BT474 cells, with apoptotic levels less than 6% (FIG. 6B). In contrast, TAE226 inhibitor (Novartis) caused higher levels of apoptosis, that were equal to 35% at 10 μM and reached 69% at 20 μM dose (FIG. 6B). Hoechst stained nuclei of Y15 and TAE226-treated cells are shown in FIG. 6C. No apoptotic nuclei were detected in Y15-treated cells at 200 μM dose in contrast to TAE226-treated cells at 20 μM doses (FIG. 6C). Since Y15 drug doesn't cause significant apoptosis at 50 and 100-200 μM doses, the mechanism of intracellular FAK kinase inhibition is independent of cellular cytotoxicity. Thus, Y15 inhibitor is not toxic and not apoptotic to cells.

To test the effect of Y15 on apoptosis, we performed Hoechst staining on untreated and Y15-treated cells. At high dose (50-100 μM), Y15 caused a small and not significant (less than 10%) increase in apoptosis in Panc-1 cells. The same effect was seen in Miapaca-2 cells. TAE226 (Novartis) caused a slightly higher level of apoptosis after 48 hours of treatment compared to similar doses of Y15. Hoechst stained nuclei of Y15 and TAE226-treated cells show no detection of apoptotic nuclei in Y15-treated cells at a 50 μM dose in contrast to TAE226-treated cells at 50 μM doses. Since Y15 does not cause significant apoptosis at high doses, the mechanism of intracellular FAK kinase inhibition is independent of apoptotic cell death.

Trypan blue staining in Panc-1 and Miapaca-2 cells shows decreased cell viability indicative of necrosis with increasing doses of Y15 (FIG. 10D). This contrasts to the effects seen in normal breast epithelial cells (MCF10A) where no decrease in cell viability is seen at doses up to 10 μM.

Example 10

Figure 6D:
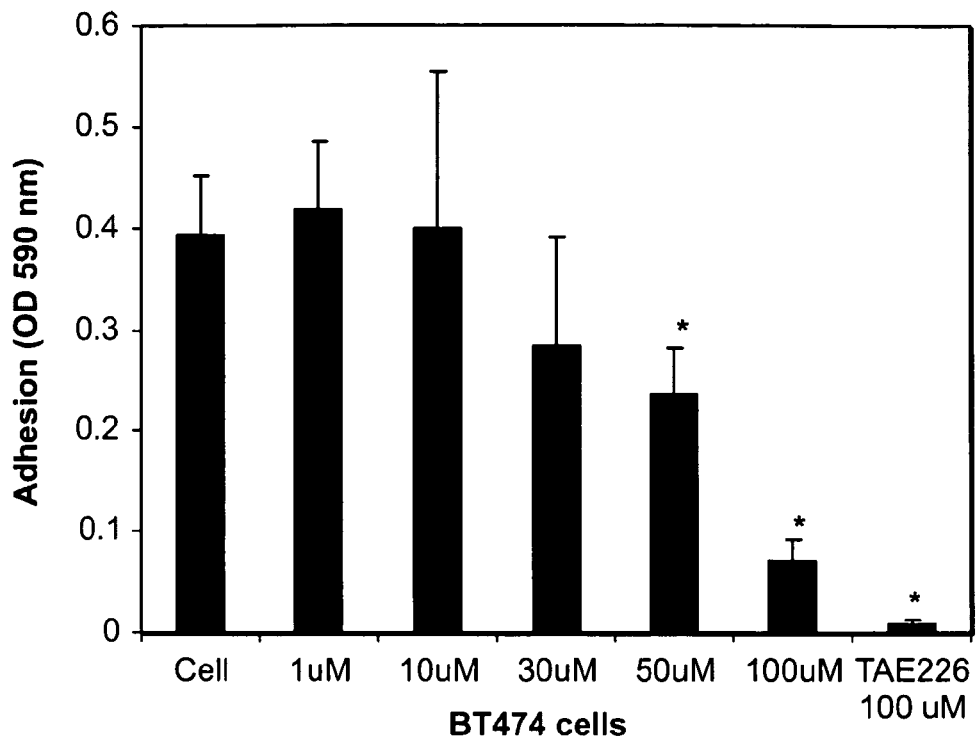
FIG. 6D illustrates that Y15 blocks cell adhesion in a dose-dependent manner.

1,2,4,5-benzenetetraamine tetrahydrochloride (Y15) Inhibits Cell Adhesion in a Dose-Dependent Manner To test the effect of Y15 on cell adhesion, we treated BT474 with different doses of Y15 and with 100 μM TAE226 on collagen-coated plates and measured adhesion. Y15 inhibited cell adhesion in a dose-dependent manner (FIG. 6D). Starting with 50 μM cell adhesion was significantly decreased that is consistent with Y397-decreased FAK phosphorylation at these doses. At 100 μM dose Y15 significantly inhibited cell adhesion as TAE-226 drug (FIG. 6D). Thus, Y15 effectively blocks cell adhesion.

To test the effect of Y15 on cell adhesion, we treated pancreatic tumor cells with different doses of Y15 and with 50 μM TAE226 on collagen-coated plates and measured adhesion. Y15 inhibited cell adhesion in a dose-dependent manner. Starting with a dose of 10 μM, cell adhesion was significantly decreased consistent with Y397-decreased FAK phosphorylation at these doses. A 50 μM dose of Y15 decreased adhesion in a similar fashion to 50 μM of TAE226. Thus, Y15 effectively blocks cell adhesion in a dose-dependent manner.

Example 11

Figure 7A:
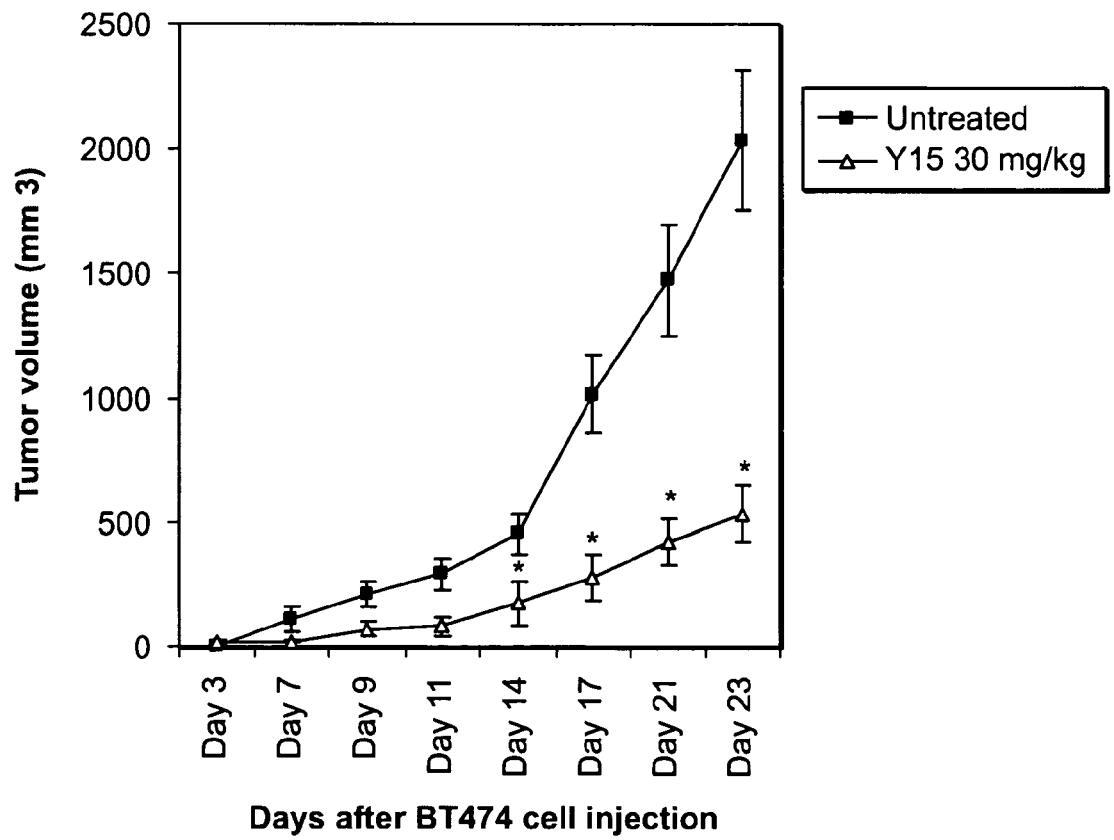
FIGS. 7A, B illustrate the effect of Y15 on tumor growth in vivo.
Figure 7C:
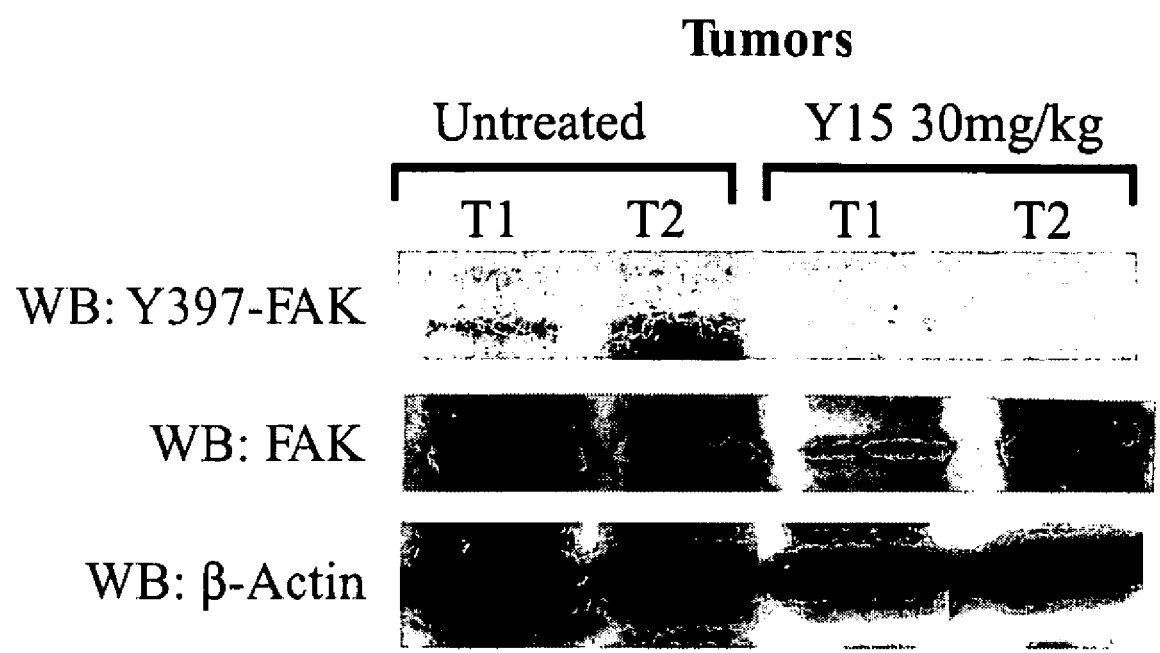
FIGS. 7C, D illustrate the results showing that Y15 decreases Y397-FAK phosphorylation in tumors.
Figure 7D:
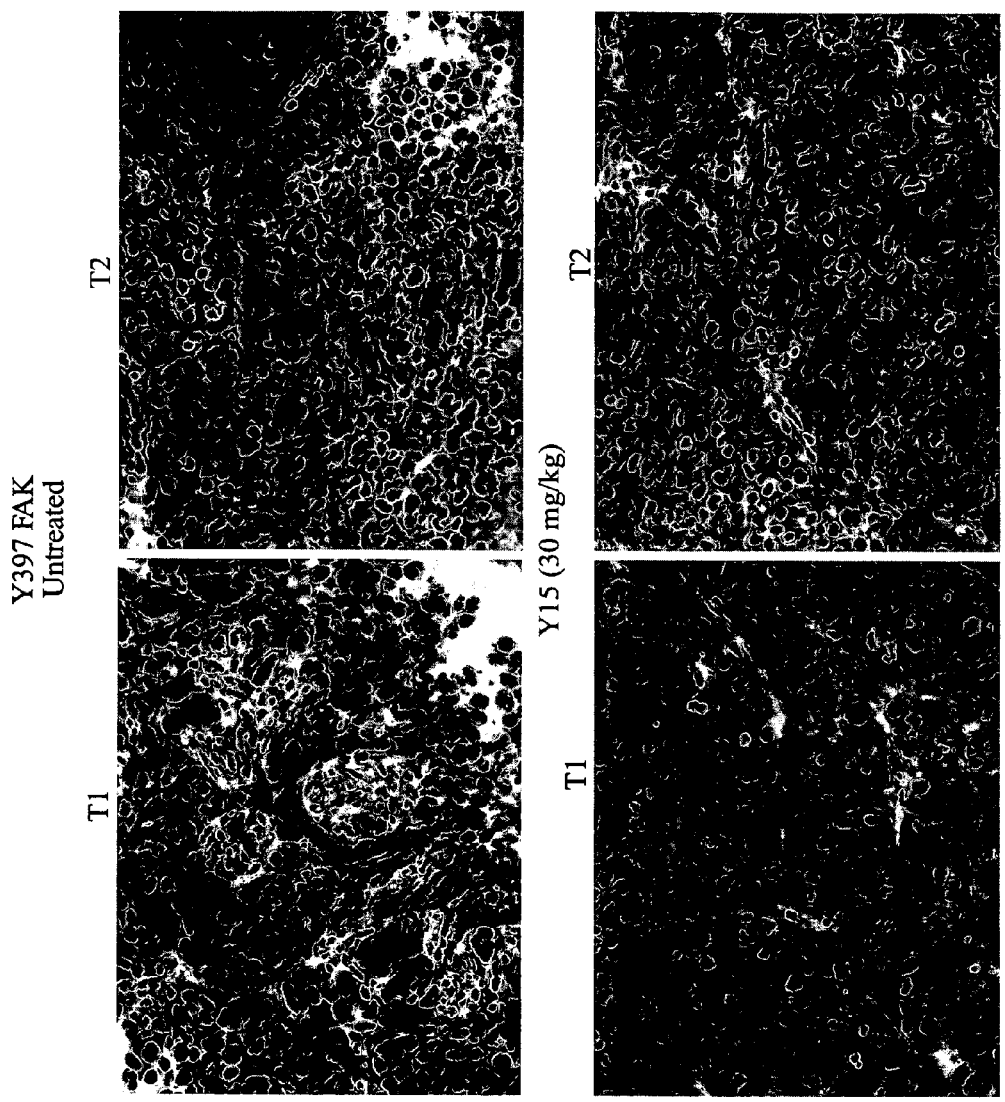
FIG. 7.

1,2,4,5-benzenetetraamine tetrahydrochloride (Y15) Inhibits Breast Tumor Growth In Vivo and Decreases Y397-FAK To detect in vivo effect of Y15 drug, we introduced BT474 cells subcutaneously into nude mice. Initially we determined that dose 30 mg/kg is the optimal dose. We treated mice with 30 mg/kg dose of Y15 for 5 days/week and compared tumor growth with untreated mice. Y15 significantly blocked tumor growth in vivo (FIG. 7A). Y15 significantly reduced tumor weight compared to untreated mice (FIG. 7B, upper panel) and tumor volume was significantly less than in untreated samples (FIG. 7B, lower panel). We isolated tumors from untreated mice and mice treated with Y15 and probed for Y397 levels by Western blotting. Tumors from untreated mice had significantly higher levels of Y397 phosphorylation than tumors treated with Y15, while total FAK levels were the same (FIG. 7C). Similar result was obtained by immunohistochemical staining of tumors with Y397 antibody (FIG. 7D). Tumors from Y15-treated mice had less Y397-FAK phosphorylation than tumors from untreated mice. Thus, Y15 significantly suppressed breast tumorigenesis that is consistent with in vitro viability and biochemical data.

Example 12

Thus, targeting Y397 of FAK with structure-based molecular docking and NCI database screening approaches revealed 36 compounds out of 20,000 different compounds that best fit in this pocket. Among these compounds 1,2,4,5-benzenetetraamine tetrahydrochloride (called Y15 compound) was the most effective in decreased cell viability in several cancer cell lines. Importantly, this compound decreased Y397 phosphorylation and total FAK phosphorylation. It directly decreased FAK autophosphorylation in vitro. Y15 decreased FAK phosphorylation in a dose- and time dependent manner and was not cytotoxic to cells, as no significant apoptosis was detected in high 100 µM doses. Y15 increased cell detachment and decreased cell adhesion. In addition in vivo, Y15 compound significantly inhibited tumor growth in BT474 breast cancer cells, subcutaneously injected in mice. Tumors from mice treated with Y15 had decreased Y397-phosphorylation of FAK. Thus, Y15 inhibitor, targeting Y397 site of FAK, can be affective in anti-cancer therapy.

Thus, this report shows that the DOCK program shows proof-of principle for using silico-based strategies for identifying novel inhibitors of FAK. This method was successfully used before for Jak2 kinase (19), but for the FAK kinase and for targeting the main phosphorylation site of FAK it was never reported. Thus, screening compounds that target other phosphorylation can also provide novel inhibitors that can be potentially used in therapy.

The molecular structure of Y15 (1,2,4,5-benzenetetraamine tetrahydrochloride) is known, and it contains a single aromatic ring. Thus, this single aromatic ring compound can serve as a potential lead compound for future chemically synthesized derivatives and novel FAK inhibitors.

The most important finding is that Y15 blocked tumorigenesis in mice in vivo, showing potential in therapy for these drugs. Two other novel FAK drugs were reported, PF-228 by Pfizer and TAE226 by Novartis. Both drugs have their own limitations; the first drug has no effect on cell viability and no report on tumorigenesis is known. The second drug has an inhibiting effect on IGFR-1, MAPK and AKT (16). Y15 drug blocked cell adhesion in a dose-dependent manner. The fact that Y15 inhibited less cell adhesion and caused less detachment than TAE226 drug, can be explained by less-specificity of TAE226 drug to FAK, as it cross-reacts with other kinases. Y15 specifically blocked Y397 phosphorylation of FAK and did not inhibit other kinases. Y15 drug blocked tumorigenesis at doses lower than TAE226. In glioma tumors TAE226 was used at 50-75 mg/kg (16). In the ovarian tumor model, TAE226 alone at 30 mg/kg was not so effective and required additional docetaxel treatment to reduce tumor growth (18). In the breast cancer model, Y15 alone effectively inhibited>74% of tumor growth at 30 mg/kg dose. Thus, developing novel, more specific inhibitors of FAK that will block tumorigenesis is important to the field.

Thus, this report led to the identification of 1,2,4,5-benzenetetraamine tetrahydrochloride, a small-molecule FAK inhibitor that directly targeted the Y397 autophosphorylation site of FAK and decreased its phosphorylation, inhibited cell viability and adhesion in vitro and blocked tumorigenesis in vivo. Thus, this compound and its derivatives may be important for future therapies.

Example 13

1,2,4,5-Benzenetetraamine tetrahydrochloride (Y15) Blocks FAK Autophosphorylation by 24 Hours Next we analyzed whether Y15 inhibits FAK Y397 phosphorylation in time-dependent manner. We treated pancreatic tumor cells with 100 µM of Y15 for 0, 1, 4, 6 and 24 hours, and then Western blotting was performed with Y397 antibody. The results demonstrate that treatment with Y15 for 6 hours or less did not significantly decrease Y397 phosphorylation, but 24 hours was enough to completely block Y397-phosphorylation and to down-regulate FAK.

Example 14

1,2,4,5-Benzenetetraamine tetrahydrochloride (Y15) Blocks ERK1/2 Phosphorylation ERK1/2 is known to be a downstream player from FAK in survival signaling. To demonstrate the effect of Y15 on FAK signaling, we tested its effect on ERK1/2 phosphorylation. The ability of Y15 to down regulate p-ERK was evaluated. Consistent with the effects of Y15 on p-FAK, p-ERK is down regulated in both cell lines in a dose dependent fashion. Similar results were seen in Miapaca-2 cells.

Example 15

1,2,4,5-Benzenetetraamine tetrahydrochloride (Y15) Causes Dose-Dependent Cell Detachment To test the cytotoxic effect of Y15 inhibitor on pancreatic cancer cells, we treated Panc-1 cells with the Y15 inhibitor at increasing doses for 24 and 48 hours. We performed analysis of detachment and apoptosis at various time points. Y15 caused a dose-dependent increase in detachment. After 48 hours with a 10 µM dose, Y15 caused 13% detachment in Panc-1 cells, while at a 50 µM dose, detachment was equal to 32%. Y15 caused more detachment than TAE226 (Novartis) inhibitor. Thus, Y15 effectively caused dose-dependent cellular detachment. Similar results were seen in Miapaca-2 cells with significant detachment starting at a dose of 3 µM. Y15, at doses up to 10 µM did not cause a significant change in morphology or increase in cell detachment in normal human fibroblasts. Therefore, both pancreatic cancer cells lines are more sensitive to Y15 induced detachment compared to normal fibroblasts.

Example 16

Figure 11A:
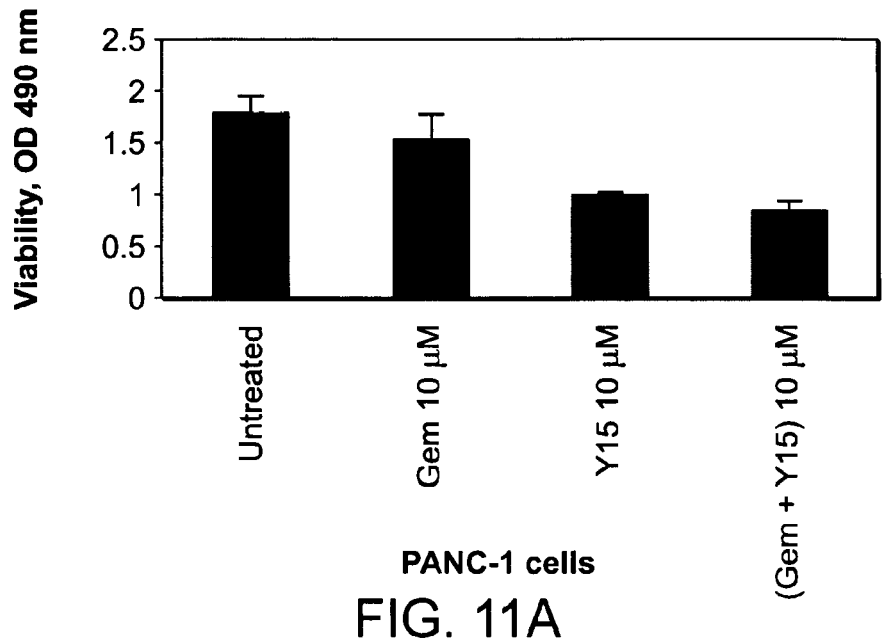
FIGS. 11A, B illustrate in vitro and in vivo effects of Y15 when combined with gemcitabine.
Figure 11B:
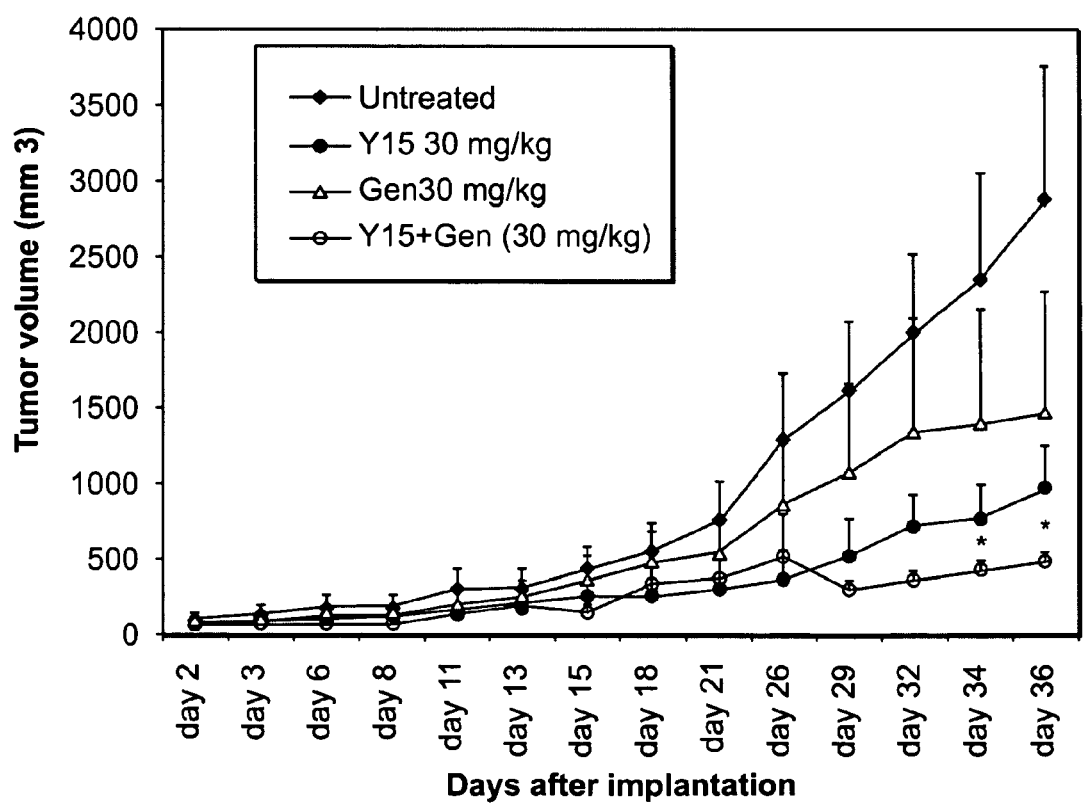
FIG. 11.

1,2,4,5-Benzenetetraamine tetrahydrochloride (Y15) Inhibits Human Pancreatic Tumor Growth In Vivo and Decreases Y397-FAK Phosphorylation Gemcitabine is considered to be the most active agent in the treatment of patients with pancreatic cancer. Thus, we evaluated pancreatic cancer cell viability in-vitro with Y15 or with gemcitabine alone or in the presence of the combination of Y15 plus gemcitabine chemotherapy. As shown in FIG. 11A, the combination of gemcitabine (10 µM) chemotherapy+Y15 (10 µM) treatment significantly decreased cell viability compared to gemcitabine (10 µM) or Y15 treatment (10 µM) alone. Following this, to evaluate the in-vivo effect of Y15, we introduced pancreatic tumor cells subcutaneously into nude mice. Initially we determined that a dose of 30 mg/kg was the optimal non-toxic dose. We treated mice with intraperitoneal Y15 (30 mg/kg) for 5 days/week and compared tumor growth to mice receiving a placebo saline control. No animal weight loss or death was observed in any tumor growth inhibition experiment for 36 days (data not shown). Next, nude mice had Panc-1 tumor cells injected into the subcutaneous position. After one week of tumor growth, animals (n=5/group) were randomized to receive daily intraperitoneal injections of PBS, Y15 alone (30 mg/kg), gemcitabine alone (30 mg/kg) or Y15 (30 mg/kg)+gemcitabine (30 mg/kg). As shown in FIG. 11B, when given alone, Y15 or gemcitabine inhibited tumor growth. Y15 inhibited tumor growth even better than gemcitabine alone. Importantly, the combination of Y15+gemcitabine treatment significantly inhibited tumor growth compared to either one alone. In addition, combined treatment with Y15+gemcitabine caused a significant decrease in tumor weight compared to the other groups. On day 36, following the last treatment, mice were sacrificed and tumors were analyzed for FAK-Y397 levels by Western blotting. Tumors from Y15 treated mice had lower levels of Y397 phosphorylation than tumors treated with PBS (control). Thus, Y15 significantly suppressed pancreatic cancer tumorigenesis and had a synergistic effect with gemcitabine chemotherapy. These findings are consistent with the in-vitro viability data.

Immunohistochemistry to evaluate caspase-3 and Ki67 were performed from tumors in all four groups. Caspase-3 staining revealed no significant increase in apoptotic cells in tumors treated with Y15 alone (6%), gemcitabine alone (2%) or Y15+gemcitabine (2%). However, Ki67 staining decreased the most in tumors treated with Y15+gemcitabine.

Figure Legends

Figure 1A:
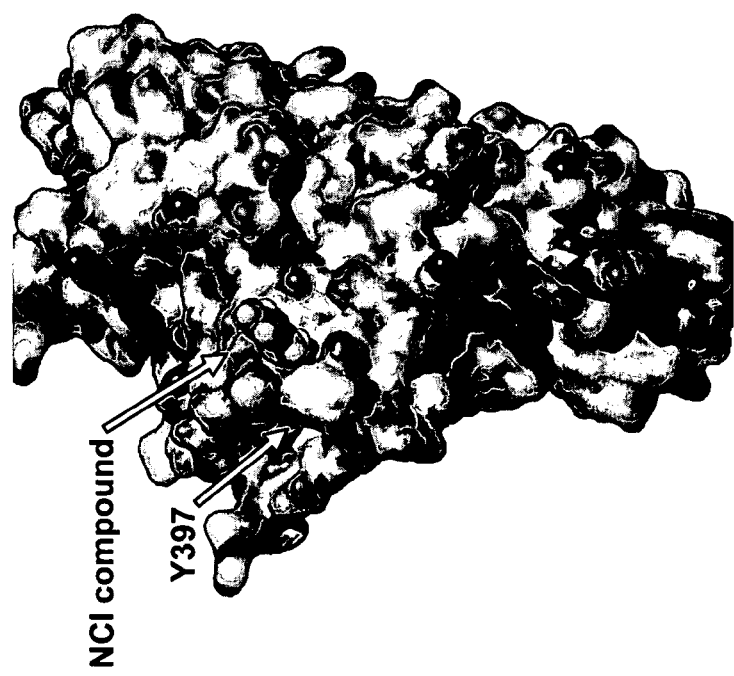

FIG. 1A, B. Targeting of Y397 site of FAK by structure-based molecular docking approach. The crystal structure of FAK (FERM) domain, reported in (20) with one of the NCI compound targeting Y397 site of FAK (shown by arrows) (A). Zoomed image of Y397 site and this example compound (B).

FIG. 2A, B. The effect of compounds targeting Y397 site on viability of breast cancer and melanoma cell lines. The 36 drugs were added to the cells for 24 hours at 100 µM dose and MTT assay was performed, as described in Materials and Methods. Known FAK inhibitor, TAE226 (Novartis), was used as a control. T47D breast cancer cell line (A and C8161 melanoma cell line (B). Bars show means±standard deviations.

FIG. 3. The structure of 1,2,4,5-benzenetetraamine tetrahydrochloride (Y15) compound. Upper panel: 1,2,4,5-benzenetetraamine tetrahydrochloride targets Y397 site of FAK. Lower panel: Chemical structure and name of the Y15 compound.

FIG. 4A, B, C, D. Y15 inhibits cell viability and decreases Y397 FAK phosphorylation in a dose-dependent manner. BT474 breast cancer cells were treated with different doses of Y15 drug for 24 hours and MTT assay was performed to test the effect on cell viability (A). Bars show means±standard deviations. Y15 inhibits cell viability in a dose-dependent manner. *P<0.05 viability of Y15-treated cells versus control untreated cells.

Y15 specifically inhibits Y397 phosphorylation of FAK. BT474 cells were treated with Y15 drug at 100 µM for 24 hours and Western blotting with Y397 and Y118 paxillin. to detect the level of phosphorylated FAK and paxillin, respectively (B). Western blotting with total FAK, paxillin and β-Actin was performed to detect expression of proteins in the cells. Y15 effectively inhibited phosphorylation of Y397 and FAK substrate, Y118-paxillin. Y15 blocked total phosphorylation of FAK (C). Immunoprecipitation was performed with FAK antibody and Western blotting with phosphotyrosine antibody was performed. The blot was stripped and probed with FAK antibody. Y15 blocked phosphorylation of FAK. Immunostaining with Y397 antibody shows decreased Y397 in cells treated with Y15 and control TAE226 (Novartis) inhibitor Y15 inhibits FAK autophosphorylation in a dose-dependent manner (D). Cells were treated with different doses of Y15 inhibitor and Western blotting was performed with Y-397 and then with FAK antibody. Western blotting with β-Actin antibody was performed to control equal protein loading.

FIG. 4E. Y15 inhibits FAK autophosphorylation in a time-dependent manner. Cells were treated with 100 µM of Y15 for 1, 1, 4, 8 and 24 hours. Treatment with TAE226 drug at 100 µM for 24 hours was used as a control. Western blotting with Y397 was performed to detect Y397-FAK level. Then the blot was stripped and Western blotting with FAK and β-Actin was performed. Y15 inhibits Y397-FAK phosphorylation in a dose-dependent manner.

FIG. 5. Y15 directly blocks in vitro kinase activity of FAK. In vitro kinase assay was performed with $\gamma$-ATP$^{32}$, 0.1 µg of purified FAK protein and different doses of Y15 drug for 10 minutes at room temperature, as described in Materials and Methods. Y15 directly blocks FAK kinase activity in a dose-dependent manner.

FIG. 6A. Y15 causes dose-dependent cell detachment in BT474 cells. BT474 cells were treated with different doses of Y15. The detachment was determined on a hemacytometer, as described in Materials and Methods. Bars show means±standard deviations in three independent experiments. Y15 significantly decreased cell detachment.

FIG. 6B. Y15 doesn't cause significant apoptosis in BT474 cells. Hoechst staining was performed on BT474 cells with different doses of Y15 and TAE226 drugs, as described in Materials and Methods. No significant apoptosis was detected with Y15 drug compared to TAE226 inhibitor. Bars represent means±standard deviations in three independent experiments. *P<0.05 versus untreated cells.

FIG. 6C. Hoechst staining of Y15-treated BT474 cells. Apoptotic nuclei stained with Hoechst are shown. No apoptotic nuclei were observed with Y15 inhibitor at 200 µM dose compared to TAE226 inhibitor at 20 µM dose.

FIG. 6D. Y15 blocks cell adhesion in a dose-dependent manner. BT474 cells were treated with Y15 drug at different concentration and cell adhesion was measured as described in Materials and Methods. TAE226 inhibitor at 100 µM was used as a control. Y15 significantly blocked cell adhesion in a dose dependent manner. Bars show means±standard errors in four independent experiments*, P<0.05, cells adhesion in Y15 treated cells less than in control untreated cells.

FIG. 7A, B. The effect of Y15 on tumor growth in vivo. BT474 breast cancer cells were subcutaneously injected in 5 mice (A). The day after injection, Y15 at 30 mg/kg was added daily 5 days per week. Five untreated mice were used as a control group. Tumor volume was measured with calipers. Y15 significantly blocked tumor growth in vivo. Bars represent means±standard deviations (n=5) P<0.05, Student's t-test.

Y15 blocked tumor weight and volume (B). At day 23 after breast cancer cell injection, tumors were extracted, and weight and volume was determined in grams (upper panel) and in mm$^3$ (lower panel), respectively. Y15 significantly blocked tumor weight (upper panel) and volume (lower panel). Bars represent means±standard deviations.

p<0.05, Student's t-test.

FIGS. 7C, D. Y15 decreases Y397-FAK phosphorylation in tumors. We isolated tumors from untreated mice and from mice, treated with Y15 drug. Cell lysates were prepared, and Western blotting was performed with Y397 antibody (C). FAK and β-actin antibodies were used for detecting total FAK and 13-Actin levels. Immunohistochemical staining analysis was performed on untreated and Y15-treated tumors with Y397-antibody (D). Two representative tumors from untreated and Y15 treated mice groups are shown (marked as T1 and T2. tumors in each group) (C, D). Y15 decreased Y397FAK in tumors treated with Y15 (30 mg/kg) compared with untreated mice.

Figure 8A:
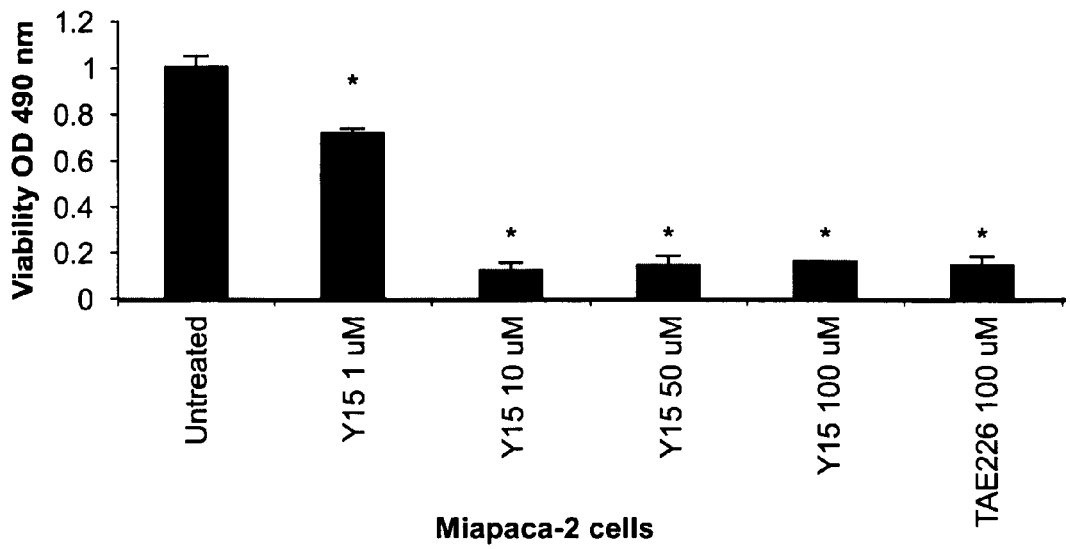
FIGS. 8A, B, C illustrate the effect of Y15 on viability of pancreatic cancer cell lines and FAK wildtype and null fibroblasts.
Figure 8B:
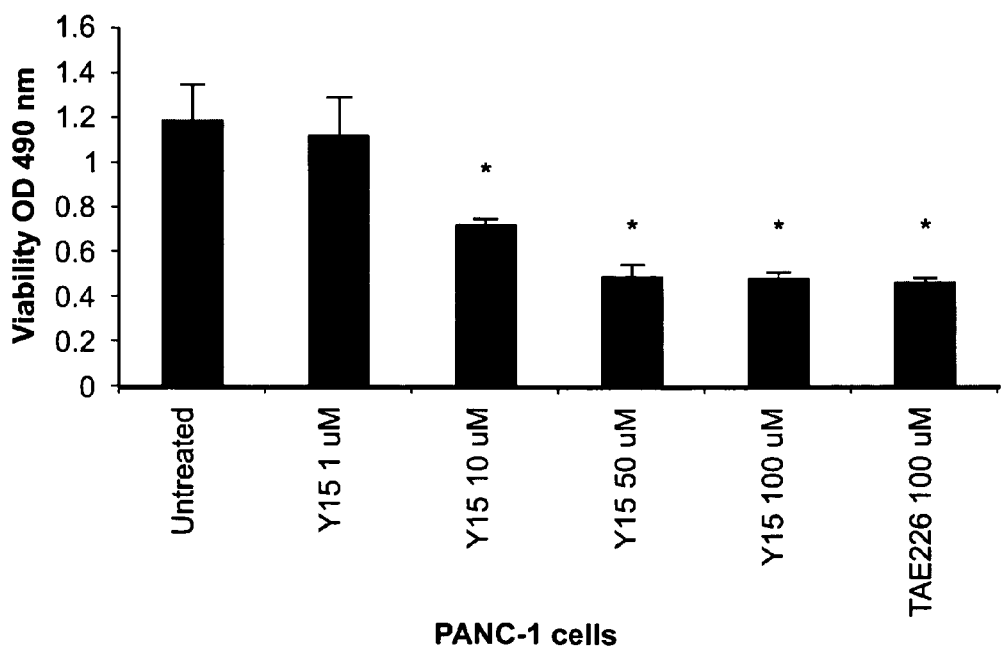
FIG. 8.
Figure 8C:
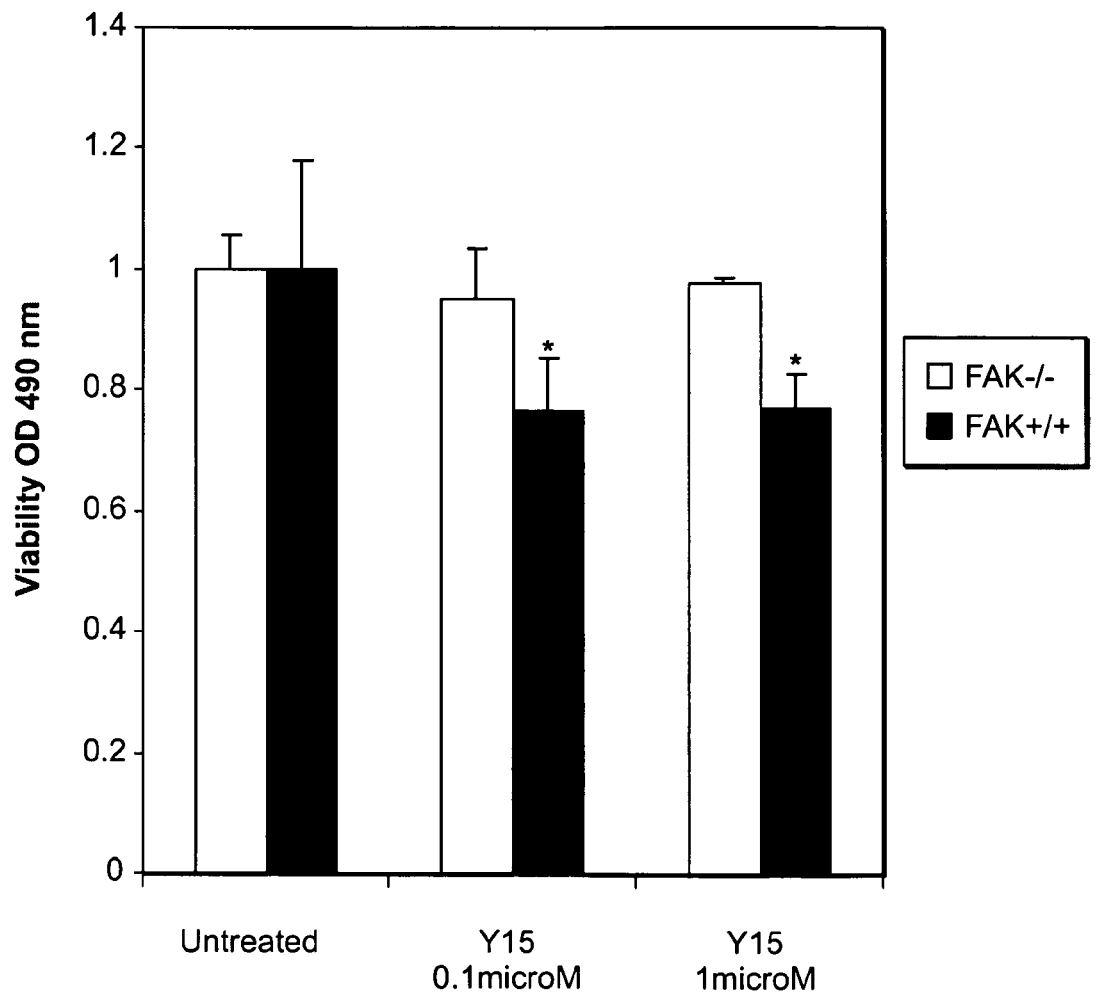

FIGS. 8A, B, C. The effect of Y15 on viability of pancreatic cancer cell lines and FAK wildtype and null fibroblasts. Y15 was added to Panc-1 (A) and Miapaca-2 (B) cells for 72 hours at increasing doses and MTT assay was performed, as described in Materials and Methods. Known FAK inhibitor, TAE226 (Novartis), was used as a control. Bars show means±standard deviations, *p<0.05 vs untreated. C. Y15 was added to FAK null and wildtype MEFs for 72 hours and MTT assay was performed. Bars show means±standard deviations, *p<0.05 vs untreated.

FIGS. 9A, B. Effect of Y15 on FAK and ERK phosphorylation (A). Cells were treated with different doses of Y15 or TAE226 inhibitor for 24 hours and Western blotting was performed with Y-397 and then with FAK antibody and antibody to p-paxillin and paxillin (B). Western blotting with β-Actin antibody was performed to control for equal protein loading. Densitometry shown below blot. Similar results were seen with Miapaca-2 cells.

Figure 10:
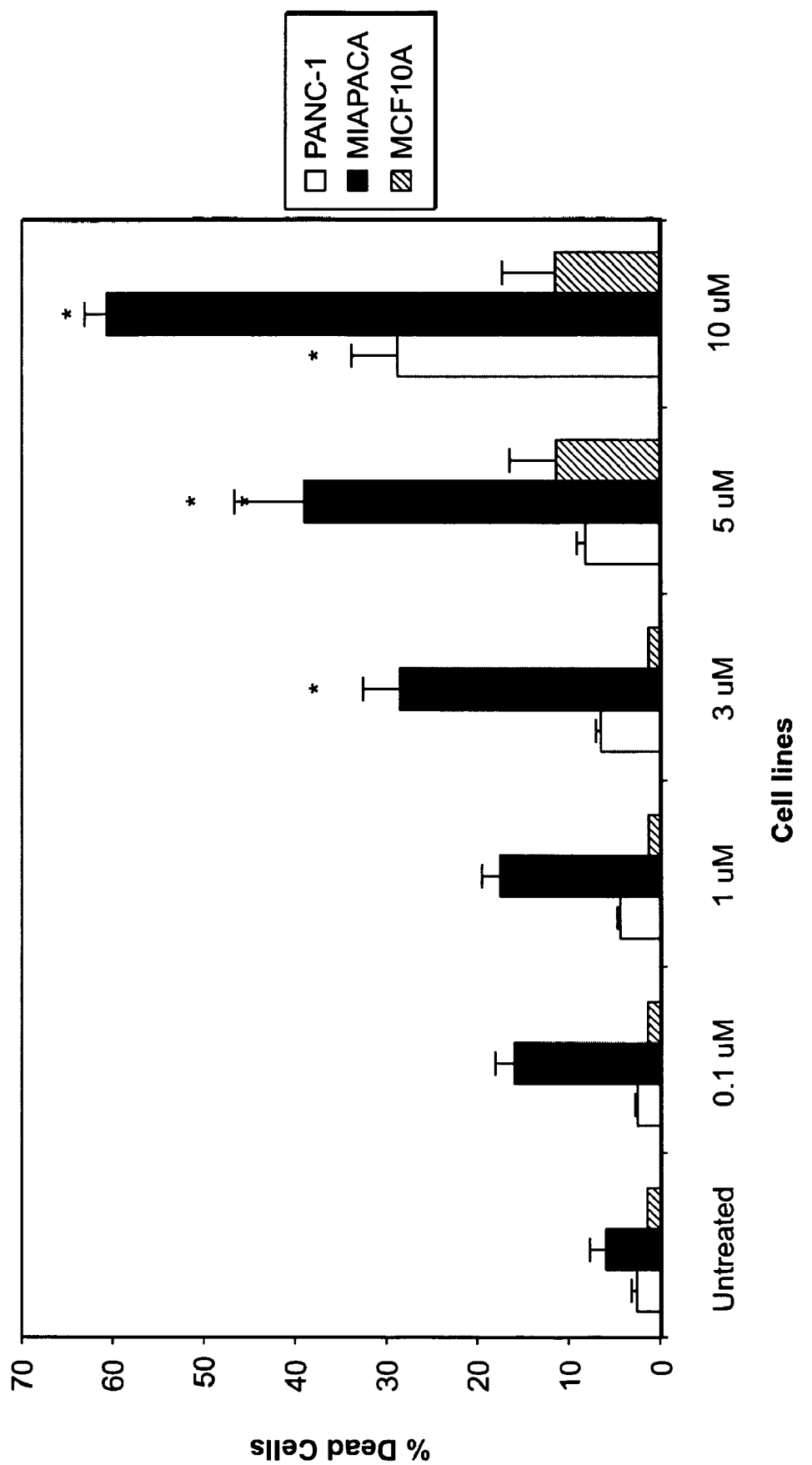
FIG. 10.

FIG. 10. Y15 causes dose-dependent cell detachment with no significant apoptosis in pancreatic cancer cells. Y15 causes a dose dependent decrease in cell viability, possibly via necrosis in pancreatic cancer cells but not tumor associated fibroblasts. Cells were treated with increasing doses of Y15 for 24 hours. Trypan blue staining showed decreased viability with no significant increase in apoptosis in pancreatic cancer cells. There was no significant decrease in viability in fibroblast cells.

FIGS. 11A, B. In vitro and in vivo effects of Y15 when combined with gemcitabine. (A). Y15 potentiates gemcitabine activity in vitro. Panc-1 cells were treated with gemcitabine alone (10 µM), Y15 alone (10 µM) or the combination of both gemcitabine (10 µM) and Y15 (10 µM) for 72 hours. Cell viability was determined by MTT assay. *p<0.05 vs Y15 or gemcitabine alone. (B). Y15 significantly blocks tumor growth in vivo and its effects are synergistic with gemcitabine treatment. Mice (n=5/group) were subcutaneously injected with Panc-1 cells. The day after injection, mice were treated with daily intraperitoneal PBS, intraperitoneal Y15 (30 mg/kg), intraperitoneal gemcitabine alone (30 mg/kg) or Y15 (30 mg/kg)+gemcitabine (30 mg/kg). The combination of Y15+gemcitabine significantly decreased tumor volume compared to Y15 or gemcitabine (Gen) alone. *p<0.05 vs Y15 or gemcitabine alone.

References
1. Schaller, M. D. (1996) *J Endocrinol* 150(1), 1-7
2. Hildebrand, J. D., Schaller, M. D., and Parsons, J. T. (1993) *Journal of Cell Biology* 123(4), 993-1005
3. Xing, Z., Chen, H. C., Nowlen, J. K., Taylor, S. J., Shalloway, D., and Guan, J. L. (1994) *Mol Biol Cell* 5(4), 413-421
4. Cobb, B. S., Schaller, M. D., Leu, T. H., and Parsons, J. T. (1994) *Molecular & Cellular Biology* 14(1), 147-155
5. Schaller, M. D., Hildebrand, J. D., Shannon, J. D., Fox, J. W., Vines, R. R., and Parsons, J. T. (1994) *Molecular & Cellular Biology* 14(3), 1680-1688
6. Hanks, S. K., and Polte, T. R. (1997) *Bioessays* 19(2), 137-145
7. Golubovskaya, V. M., and Cance, W. G. (2007) *Int Rev Cytol* 263, 103-153
8. Smith, C. S., Golubovskaya, V. M., Peck, E., Xu, L. H., Monia, B. P., Yang, X., and Cance, W. G. (2005) *Melanoma Res* 15(5), 357-362
9. Xu, L.-h., Yang, X.-h., Bradham, C. A., Brenner, D. A., Baldwin, A. S., Craven, R. J., and Cance, W. G. (2000) *J. Biol. Chem.* 275, 30597-30604
10. Golubovskaya, V., Beviglia, L., Xu, L. H., Earp, H. S., 3rd, Craven, R., and Cance, W. (2002) *J Biol Chem* 277(41), 38978-38987
11. Halder, J., Landen, C. N., Jr., Lutgendorf, S. K., Li, Y., Jennings, N. B., Fan, D., Nelkin, G. M., Schmandt, R., Schaller, M. D., and Sood, A. K. (2005) *Clin Cancer Res* 11(24 Pt 1), 8829-8836
12. Beierle, E. A., Trujillo, A., Nagaram, A., Kurenova, E. V., Finch, R., Ma, X., Vella, J., Cance, W. G., and Golubovskaya, V. M. (2007) *J Biol Chem* 282(17), 12503-12516
13. McLean, G. W., Carragher, N, O., Avizienyle, E., Evans, J., Brunton, V. G., and Frame, M. C. (2005) *Nat Rev Cancer* 5(7), 505-515
14. van Nimwegen, M. J., and van de Water, B. (2006) *Biochem Pharmacol*
15. Golubovskaya, V. M., Virnig, C., and Cance, W. G. (2007) *Mol Carcinog*
16. Liu, T. J., LaFortune, T., Honda, T., Ohmori, O., Hatakeyama, S., Meyer, T., Jackson, D., de Groot, J., and Yung, W. K. (2007) *Mol Cancer Ther* 6(4), 1357-1367
17. Slack-Davis, J. K., Martin, K. H., Tilghman, R. W., Iwanicki, M., Ung, E. J., Autry, C., Luzzio, M. J., Cooper, B., Kath, J. C., Roberts, W. G., and Parsons, J. T. (2007) *J Biol Chem* 282(20), 14845-14852
18. Halder, J., Lin, Y. G., Merritt, W. M., Spannuth, W. A., Nick, A. M., Honda, T., Kamat, A. A., Han, L. Y., Kim, T. J., Lu, C., Tari, A. M., Bornmann, W., Fernandez, A., Lopez-Berestein, G., and Sood, A. K. (2007) *Cancer Res* 67(22), 10976-10983
19. Sandberg, E. M., Ma, X., He, K., Frank, S. J., Ostrov, D. A., and Sayeski, P. P. (2005) *J Med Chem* 48(7), 2526-2533
20. Ceccarelli, D. F., Song, H. K., Poy, F., Schaller, M. D., and Eck, M. J. (2006) *J Biol Chem* 281(1), 252-259
21. Golubovskaya, V. M., Finch, R., Kweh, F., Massoll, N. A., Campbell-Thompson, M., Wallace, M. R., and Cance, W. G. (2007) *Mol Carcinog*, September 11 [Epub]
22. Golubovskaya, V. M., Finch, R., and Cance, W. G. (2005) *J Biol Chem* 280(26), 25008-25021

The disclosures of each and every patent, patent application and publication cited herein are hereby incorporated herein by reference in their entirety.

The recitation of a listing of chemical groups in any definition of a variable herein includes definitions of that variable as any single group or combination of listed groups. The recitation of an embodiment for a variable herein includes that embodiment as any single embodiment or in combination with any other embodiments or portions thereof.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

What is claimed is:

1. A method of inducing apoptosis in a cancer cell that expresses FAK in a subject comprising administering to the subject identified as in need thereof a compound capable of inhibiting Y397 phosphorylation of FAK;
   wherein the compound is:
   Y15: 1, 2, 4, 5-benzenetetraamine tetrahydrochloride.

2. The method of claim 1, wherein compound is capable of decreasing Y397-FAK phosphorylation in tumors.

3. The method of claim 2, wherein the compound decreases FAK autophosphorylation in vitro.

4. The method of claim 2, wherein the compound decreases FAK autophosphorylation in vivo.

5. The method of claim 4, wherein the compound has an inhibiting effect on FAK autophosphorylation at least 2 times greater than its inhibiting effect on other kinases.

6. The method of claim 5, wherein the kinase is IGFR-1, MAPK, or AKT.

7. The method of claim 2, wherein the cancer is breast, colon, pancreatic, thyroid, lung, or melanoma.

8. A method of inhibiting a FAK phosphorylation in a subject identified as in need of such treatment, comprising administering a compound identified as capable of inhibiting Y397 phosphorylation of FAK;

wherein the compound is:

Y15: 1, 2, 4, 5-benzenetetraamine tetrahydrochloride.

9. A method of treating cancer that expresses FAK in a subject comprising administering to the subject identified as in need thereof a compound capable of inhibiting Y397 phosphorylation of FAK;

wherein the compound is:

Y15: 1, 2, 4 5-benzenetetraamine tetrahydrochloride.

10. The method of claim 9, wherein the inhibiting Y397 phosphorylation of FAK results in modulation of apoptosis or cellular proliferation of cancer cells.

11. The method of claim 9, wherein the cancer is breast, colon, pancreatic, thyroid, lung, or melanoma.

12. A method of treating cancer that expresses FAK in a subject comprising administering to the subject a compound identified as capable of inhibiting Y397 phosphorylation of FAK and an additional therapeutic agent;

wherein the compound is:

Y15: 1, 2, 4, 5-benzenetetraamine tetrahydrochloride.

13. The method of claim 12, wherein the cancer is breast, colon, pancreatic, thyroid, lung, or melanoma.

14. The method of claim 12, wherein the compound identified as capable of inhibiting Y397 phosphorylation of FAK is 1, 2, 4, 5-benzenetetraamine tetrahydrochloride and the additional therapeutic agent is gemcitabine.

* * * * *